US009347886B2

(12) United States Patent
Voronov et al.

(10) Patent No.: US 9,347,886 B2
(45) Date of Patent: May 24, 2016

(54) APPARATUS FOR MONITORING DEPOSITION RATE, APPARATUS PROVIDED WITH THE SAME FOR DEPOSITING ORGANIC LAYER, METHOD OF MONITORING DEPOSITION RATE, AND METHOD OF MANUFACTURING ORGANIC LIGHT EMITTING DISPLAY APPARATUS USING THE SAME

(71) Applicant: SAMSUNG DISPLAY CO., LTD., Yongin, Gyeonggi-Do (KR)

(72) Inventors: Alexander Voronov, Yongin (KR); Dmitry Maslov, Yongin (KR); Gyoo-Wan Han, Yongin (KR)

(73) Assignee: Samsung Display Co., Ltd., Yongin-si (KR)

(*) Notice: Subject to any disclaimer, the term of this patent is extended or adjusted under 35 U.S.C. 154(b) by 137 days.

(21) Appl. No.: 14/079,522

(22) Filed: Nov. 13, 2013

(65) Prior Publication Data

US 2014/0377890 A1    Dec. 25, 2014

(30) Foreign Application Priority Data

Jun. 24, 2013    (KR) .................. 10-2013-0072706

(51) Int. Cl.
*H01L 21/66*    (2006.01)
*G01N 21/64*    (2006.01)
(Continued)

(52) U.S. Cl.
CPC ............ *G01N 21/6489* (2013.01); *C23C 14/24* (2013.01); *C23C 14/547* (2013.01); *C23C 14/568* (2013.01)

(58) Field of Classification Search
None
See application file for complete search history.

(56) References Cited

U.S. PATENT DOCUMENTS 4,059,067 A    11/1977    Lardon et al.
4,468,648 A    8/1984    Uchikune
(Continued)

FOREIGN PATENT DOCUMENTS

CN    1704501 A    12/2005
CN    1841696 A    10/2006
(Continued)

OTHER PUBLICATIONS

De Hoffmann, Edmond, Special Feature: Tutorial Tandem Mass Spectrometry: a Primer, journal, Dec. 8, 1995, 9 pages, vol. 31, 129-137, John Wiley & Sons, Ltd.
(Continued)

*Primary Examiner* — Angel Roman
(74) *Attorney, Agent, or Firm* — Lewis Roca Rothgerber Christie LLP

(57) ABSTRACT

An apparatus for monitoring deposition rate, an apparatus including the same, for depositing an organic layer, a method of monitoring deposition rate, and a method of manufacturing an organic light emitting display apparatus using the same, are provided. The deposition rate monitoring apparatus for measuring deposition rate of a deposition material discharged from a deposition source, includes: a light source for irradiating light having a wavelength within a photoexcitation bandwidth of the deposition material; a first optical system for irradiating the light emitted from the light source toward the discharged deposition material; a second optical system for collecting the light emitted from the deposition material; and a first light sensor for detecting the amount of the light which is emitted from the deposition material and collected in the second optical system.

9 Claims, 11 Drawing Sheets

(51) Int. Cl.

| | |
|---|---|
| *C23C 14/24* | (2006.01) |
| *C23C 14/54* | (2006.01) |
| *C23C 14/56* | (2006.01) |

(56) References Cited

U.S. PATENT DOCUMENTS

| | | |
|---|---|---|
| 5,487,609 A | 1/1996 | Asada |
| 5,909,995 A | 6/1999 | Wolf et al. |
| 6,274,198 B1 | 8/2001 | Dautartas |
| 6,371,451 B1 | 4/2002 | Choi |
| 6,483,690 B1 | 11/2002 | Nakajima et al. |
| 6,749,906 B2 | 6/2004 | Van Slyke |
| 6,995,035 B2 | 2/2006 | Cok et al. |
| 7,199,520 B2 | 4/2007 | Fujii et al. |
| 7,964,037 B2 | 6/2011 | Fukuda et al. |
| 2001/0006827 A1 | 7/2001 | Yamazaki et al. |
| 2002/0033136 A1 | 3/2002 | Savage et al. |
| 2002/0076847 A1 | 6/2002 | Yamada et al. |
| 2002/0168577 A1 | 11/2002 | Yoon |
| 2002/0194727 A1 | 12/2002 | Cho et al. |
| 2003/0101937 A1 | 6/2003 | Van Slyke et al. |
| 2003/0151637 A1 | 8/2003 | Nakamura et al. |
| 2003/0168013 A1 | 9/2003 | Freeman et al. |
| 2003/0193672 A1* | 10/2003 | Okada et al. ............... 356/630 |
| 2003/0221614 A1 | 12/2003 | Kang et al. |
| 2003/0232563 A1 | 12/2003 | Kamiyama et al. |
| 2004/0123804 A1 | 7/2004 | Yamazaki et al. |
| 2004/0127066 A1 | 7/2004 | Jung |
| 2004/0134428 A1 | 7/2004 | Sasaki et al. |
| 2004/0142108 A1 | 7/2004 | Atobe et al. |
| 2004/0144321 A1 | 7/2004 | Grace et al. |
| 2004/0194702 A1 | 10/2004 | Sasaki et al. |
| 2004/0263547 A1 | 12/2004 | Sugahara |
| 2004/0263771 A1 | 12/2004 | Jeong et al. |
| 2005/0005848 A1* | 1/2005 | Yamazaki et al. ........... 118/719 |
| 2005/0016461 A1 | 1/2005 | Klug et al. |
| 2005/0031836 A1 | 2/2005 | Hirai |
| 2005/0037136 A1 | 2/2005 | Yamamoto |
| 2005/0166842 A1 | 8/2005 | Sakamoto |
| 2005/0244570 A1* | 11/2005 | Tanase et al. .................. 427/10 |
| 2005/0263074 A1 | 12/2005 | Masuda et al. |
| 2006/0102078 A1 | 5/2006 | Fairbairn et al. |
| 2006/0144325 A1 | 7/2006 | Jung et al. |
| 2006/0164786 A1 | 7/2006 | Kobayashi et al. |
| 2006/0174829 A1 | 8/2006 | An et al. |
| 2006/0185588 A1* | 8/2006 | Nozawa et al. ............... 118/712 |
| 2006/0205101 A1 | 9/2006 | Lee et al. |
| 2006/0255722 A1 | 11/2006 | Imanishi |
| 2006/0278522 A1 | 12/2006 | Kim et al. |
| 2006/0278945 A1 | 12/2006 | Sakurai |
| 2007/0009652 A1 | 1/2007 | Manz et al. |
| 2007/0046913 A1 | 3/2007 | Shibazaki |
| 2007/0077358 A1 | 4/2007 | Jeong et al. |
| 2007/0100580 A1* | 5/2007 | Marcus et al. ................. 702/170 |
| 2007/0178708 A1 | 8/2007 | Ukigaya |
| 2007/0275497 A1 | 11/2007 | Kwack et al. |
| 2007/0297887 A1 | 12/2007 | Tanaka |
| 2008/0018236 A1 | 1/2008 | Arai et al. |
| 2008/0115729 A1 | 5/2008 | Oda et al. |
| 2008/0131587 A1 | 6/2008 | Boroson et al. |
| 2008/0216741 A1 | 9/2008 | Ling et al. |
| 2008/0286461 A1 | 11/2008 | Noguchi et al. |
| 2008/0298947 A1 | 12/2008 | Yeo et al. |
| 2009/0017192 A1 | 1/2009 | Matsuura |
| 2009/0153033 A1 | 6/2009 | Lee et al. |
| 2009/0169868 A1 | 7/2009 | Haglund, Jr. et al. |
| 2009/0229524 A1 | 9/2009 | Kim et al. |
| 2009/0232976 A1 | 9/2009 | Yoon et al. |
| 2009/0304924 A1 | 12/2009 | Gadgil |
| 2009/0308317 A1 | 12/2009 | Sone et al. |
| 2009/0315456 A1 | 12/2009 | Furukawa et al. |
| 2010/0130020 A1 | 5/2010 | Kim et al. |
| 2010/0156279 A1 | 6/2010 | Tamura et al. |
| 2011/0042659 A1 | 2/2011 | Kim et al. |
| 2011/0189380 A1* | 8/2011 | Jang et al. ..................... 427/10 |
| 2011/0212256 A1 | 9/2011 | Beck et al. |
| 2011/0241438 A1 | 10/2011 | Kim et al. |
| 2014/0106062 A1* | 4/2014 | Forrest et al. ..................... 427/9 |

FOREIGN PATENT DOCUMENTS

| | | |
|---|---|---|
| EP | 1 413 644 A2 | 4/2004 |
| EP | 1 418 250 A2 | 5/2004 |
| EP | 1 518 940 A1 | 3/2005 |
| JP | 04-272170 | 9/1992 |
| JP | 1993-022405 U | 3/1993 |
| JP | 10-120171 | 5/1998 |
| JP | 2000-068054 | 3/2000 |
| JP | 2000-294372 A | 10/2000 |
| JP | 2001-028325 A | 1/2001 |
| JP | 2001-052862 A | 2/2001 |
| JP | 2001-093667 A | 4/2001 |
| JP | 2002-175878 A | 6/2002 |
| JP | 2003-003250 A | 1/2003 |
| JP | 2003-077662 A | 3/2003 |
| JP | 2003-157973 A | 5/2003 |
| JP | 2003-279326 A | 10/2003 |
| JP | 2003-297562 A | 10/2003 |
| JP | 2003-347394 A | 12/2003 |
| JP | 2004-043898 A | 2/2004 |
| JP | 2004-103269 A | 4/2004 |
| JP | 2004-103341 A | 4/2004 |
| JP | 2004-199919 A | 7/2004 |
| JP | 2004-228006 A | 8/2004 |
| JP | 2004-342455 A | 12/2004 |
| JP | 2005-044592 A | 2/2005 |
| JP | 2005-213616 A | 8/2005 |
| JP | 2005-235568 A | 9/2005 |
| JP | 2005-293968 A | 10/2005 |
| JP | 2005-296737 A | 10/2005 |
| JP | 2006-016660 A | 1/2006 |
| JP | 2006-275433 A | 10/2006 |
| JP | 2006-307247 A | 11/2006 |
| JP | 2007-047293 A | 2/2007 |
| JP | 2008-019477 A | 1/2008 |
| JP | 2008-121098 A | 5/2008 |
| JP | 2009-019243 A | 1/2009 |
| JP | 2009-87910 A | 4/2009 |
| JP | 2009-117231 A | 5/2009 |
| JP | 2010-159167 A | 7/2010 |
| KR | 1997-0008709 A | 3/1997 |
| KR | 10-0257219 B1 | 2/2000 |
| KR | 10-2000-0019254 A | 4/2000 |
| KR | 10-2000-0023929 A | 5/2000 |
| KR | 10-2001-0059939 A | 7/2001 |
| KR | 10-2002-0000201 A | 1/2002 |
| KR | 10-2002-0050922 A | 6/2002 |
| KR | 10-2002-0088662 A | 11/2002 |
| KR | 10-2002-0090934 A | 12/2002 |
| KR | 10-2003-0043012 A | 6/2003 |
| KR | 10-0405080 B1 | 11/2003 |
| KR | 10-0406059 A | 11/2003 |
| KR | 10-2003-0091947 A | 12/2003 |
| KR | 10-2003-0093959 A | 12/2003 |
| KR | 10-2004-0034537 A | 4/2004 |
| KR | 10-0430336 A1 | 5/2004 |
| KR | 10-2004-0050045 A | 6/2004 |
| KR | 10-2004-0069281 A | 8/2004 |
| KR | 10-2004-0084747 A | 10/2004 |
| KR | 10-0463212 B1 | 12/2004 |
| KR | 10-2005-0024324 A | 3/2005 |
| KR | 10-0520159 B1 | 10/2005 |
| KR | 10-2006-0008602 A | 1/2006 |
| KR | 10-2006-0018745 A | 3/2006 |
| KR | 10-2006-0073367 A | 6/2006 |
| KR | 10-2006-0077887 A | 7/2006 |
| KR | 10-2006-0080475 A | 7/2006 |
| KR | 10-2006-0080481 A | 7/2006 |
| KR | 10-2006-0080482 A | 7/2006 |
| KR | 10-2006-0083510 A | 7/2006 |
| KR | 10-2009-0097453 A | 9/2006 |
| KR | 10-2006-0104675 A | 10/2006 |
| KR | 10-2006-0104677 A | 10/2006 |
| KR | 10-2006-0109627 A | 10/2006 |

(56) References Cited

FOREIGN PATENT DOCUMENTS

| | | |
|---|---|---|
| KR | 10-0646160 B1 | 11/2006 |
| KR | 10-0687007 B1 | 2/2007 |
| KR | 10-2007-0025164 A | 3/2007 |
| KR | 10-0696547 B1 | 3/2007 |
| KR | 10-0698033 B1 | 3/2007 |
| KR | 10-0700466 B1 | 3/2007 |
| KR | 10-2007-0035796 A | 4/2007 |
| KR | 10-0711885 B1 | 4/2007 |
| KR | 10-2007-0050793 A | 5/2007 |
| KR | 10-0723627 B1 | 5/2007 |
| KR | 10-2007-0056190 A | 6/2007 |
| KR | 10-0726132 B1 | 6/2007 |
| KR | 10-0736218 B1 | 7/2007 |
| KR | 10-0741142 B1 | 7/2007 |
| KR | 10-2007-0078713 A | 8/2007 |
| KR | 10-2007-0080635 A | 8/2007 |
| KR | 10-2007-0091437 A | 9/2007 |
| KR | 10-2007-0101842 A | 10/2007 |
| KR | 10-2007-0105595 A | 10/2007 |
| KR | 10-0770653 B1 | 10/2007 |
| KR | 10-2008-0001184 A | 1/2008 |
| KR | 10-2008-0007896 A | 1/2008 |
| KR | 10-2008-0009285 A | 1/2008 |
| KR | 10-0797787 B1 | 1/2008 |
| KR | 10-0800125 B1 | 1/2008 |
| KR | 10-0823508 B1 | 4/2008 |
| KR | 10-2008-0044239 A | 5/2008 |
| KR | 10-2008-0046761 A | 5/2008 |
| KR | 10-0827760 B1 | 5/2008 |
| KR | 10-2008-0057159 A | 6/2008 |
| KR | 10-0839380 B1 | 6/2008 |
| KR | 10-2008-0060400 A | 7/2008 |
| KR | 10-2008-0061132 A | 7/2008 |
| KR | 10-2008-0062212 A | 7/2008 |
| KR | 10-2008-0076574 A | 8/2008 |
| KR | 10-2008-0104479 A | 12/2008 |
| KR | 10-2008-0104695 A | 12/2008 |
| KR | 10-2009-0038733 A | 4/2009 |
| KR | 10-0899279 B1 | 5/2009 |
| KR | 10-2009-0066996 A | 6/2009 |
| KR | 10-2009-0075887 A | 7/2009 |
| KR | 10-2009-0079765 A | 7/2009 |
| KR | 10-2009-0081717 A | 7/2009 |
| KR | 10-2009-0094911 A | 9/2009 |
| KR | 10-2010-0038088 A | 4/2010 |
| KR | 10-2010-0044606 A | 4/2010 |
| KR | 10-2010-0128589 A | 12/2010 |
| KR | 10-1017654 B1 | 2/2011 |
| KR | 10-2011-0110525 A | 10/2011 |
| KR | 10-1157322 B1 | 6/2012 |
| WO | WO 03/043067 A1 | 5/2003 |
| WO | WO 2004/016406 A1 | 2/2004 |

OTHER PUBLICATIONS

King, William H. Jr., Piezoelectric Sorption Detector, journal, Aug. 1964, 5 pages, vol. 36, No. 9, Analytical Research Division, Esso Research and Engineering Co., Linden, New Jersey, USA.
Chinese Office Action dated Oct. 9, 2012, for corresponding Chinese Patent Application No. 2010-10266406.6, 6 pages.
English Abstract, Publication No. 1020080002189, dated Jan. 4, 2008, for corresponding Korean Patent 10-0800125 listed above.
European Search Report dated May 27, 2011, for corresponding European Patent application 10251514.5, 11 pages.
KIPO Notice of Allowance dated Apr. 26, 2012, for Korean Patent application 10-2010-0066991, (5 pages).
KIPO Office action dated Apr. 9, 2012, for Korean priority Patent application 10-2010-0031556, (4 pages).
KIPO Office action dated Feb. 6, 2012, for Korean Patent application 10-2010-0011481, 7 pages.
KIPO Office action dated Feb. 6, 2012, for Korean Patent application 10-2010-0011480, 8 pages.
KIPO Registration Determination Certificate dated Jul. 2, 2012, for Korean Patent application 10-2010-0011480, (5 pages).
KIPO Registration Determination Certificate dated Jul. 2, 2012, for Korean priority Patent application 10-2010-0011481, (5 pages).
Korean Patent Abstracts, Publication No. 10-0151312 B1, dated Jun. 18, 1998, corresponding to Korean Publication 1997-0008709 listed above.
Korean Patent Abstracts, Publication No. 1020010062735, dated Jul. 7, 2001, for corresponding Korean Patent 10-0827760 listed above.
Korean Patent Abstracts, Publication No. 1020020034272, dated May 9, 2002, for corresponding Korean Patent 10-0726132 listed above.
Korean Patent Abstracts, Publication No. 1020020056238, dated Jul. 10, 2002, for corresponding Korean Patent 10-0698033 listed above.
Korean Patent Abstracts, Publication No. 1020020086047, dated Nov. 18, 2002, for corresponding Korean Patent 10-0405080 listed above.
Korean Patent Abstracts, Publication No. 1020020088662, dated Nov. 29, 2002, for corresponding Korean Patent 10-0463212 listed above.
Korean Patent Abstracts, Publication No. 1020040062203, dated Jul. 7, 2002, for corresponding Korean Patent 10-0646160 listed above.
Korean Patent Abstracts, Publication No. 1020050045619, dated May 17, 2005, for corresponding Korean Patent 10-0520159 listed above.
Korean Patent Abstracts, Publication No. 1020050078637, dated Aug. 5, 2005, for corresponding Korean Patent 10-0700466 listed above.
Korean Patent Abstracts, Publication No. 1020060101987, dated Sep. 27, 2006, for corresponding Korean Patent 10-0687007 listed above.
Korean Patent Abstracts, Publication No. 1020060126267, dated Dec. 6, 2006, for corresponding Korean Patent 10-0797787 listed above.
Korean Patent Abstracts, Publication No. 1020070025164, dated Mar. 8, 2007, for corresponding Korean Patent 10-0711885 listed above.
Korean Patent Abstracts, Publication No. 10-2007-0056241, dated Jun. 4, 2007, corresponding to Korean Patent 10-0741142 B1 listed above.
Korean Patent Abstracts, Publication No. 1020080038650, dated May 7, 2008, for corresponding Korean Patent 10-0839380 listed above.
Korean Patent Abstracts, Publication No. 10-2008-0070302, dated Jul. 30, 2008, corresponding to Korean Patent 10-0899279 B1 listed above.
Patent Abstracts of Japan, and English machine translation of Japanese Publication 2001-052862, 20 pages.
Patent Abstracts of Japan, and English machine translation of Japanese Publication 2003-003250, 25 pages.

* cited by examiner

FIG. 10
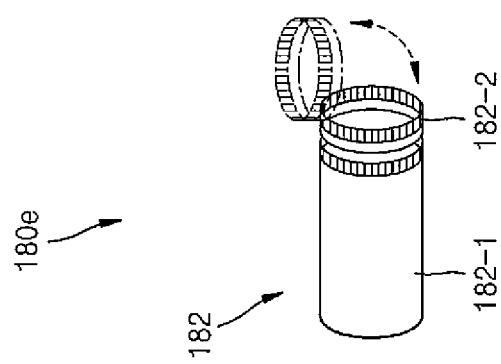
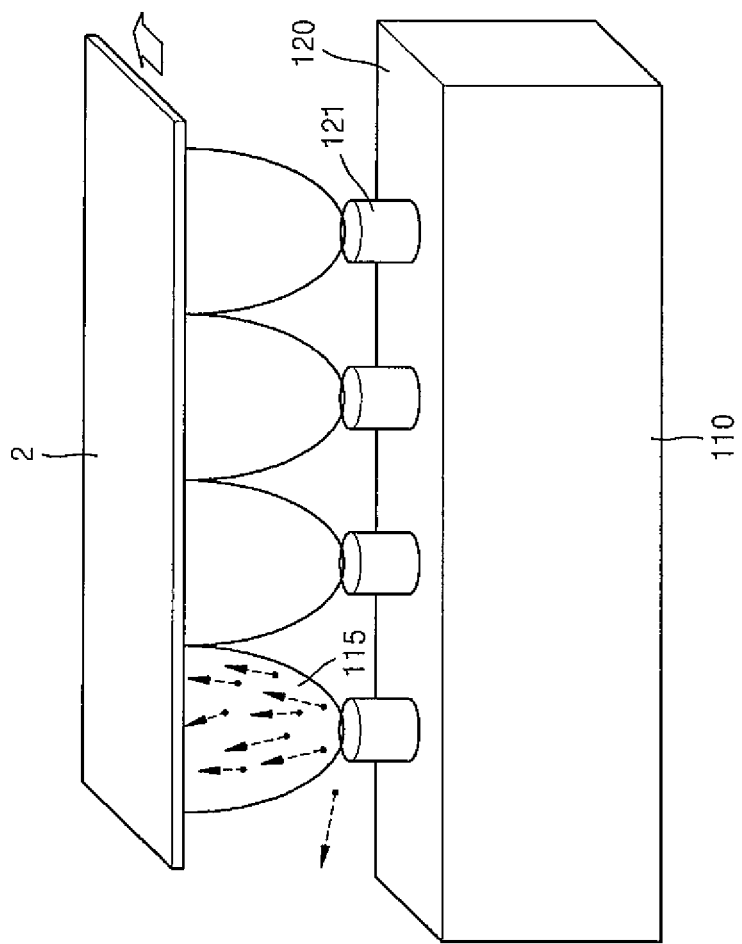

APPARATUS FOR MONITORING DEPOSITION RATE, APPARATUS PROVIDED WITH THE SAME FOR DEPOSITING ORGANIC LAYER, METHOD OF MONITORING DEPOSITION RATE, AND METHOD OF MANUFACTURING ORGANIC LIGHT EMITTING DISPLAY APPARATUS USING THE SAME

CROSS-REFERENCE TO RELATED APPLICATION

This application claims priority to and the benefit of Korean Patent Application No. 10-2013-0072706, filed on Jun. 24, 2013, in the Korean Intellectual Property Office, the disclosure of which is incorporated herein in its entirety by reference.

BACKGROUND

1. Field

One or more embodiments of the present invention relate to an apparatus for monitoring deposition rate, an apparatus provided with the same, for depositing an organic layer, a method of monitoring deposition rate, and a method of manufacturing an organic light emitting display apparatus using the same.

2. Description of the Related Art

Among various display apparatuses, an organic light-emitting display apparatus has wide viewing angles, good contrast, and a fast response speed, and has gotten the attention as a next generation display apparatus.

An organic light-emitting display apparatus includes an intermediate layer between first and second electrodes facing each other, and the intermediate layer includes a light-emitting layer. In this regard, the electrodes and the intermediate layer may be formed by various methods, for example, an independent deposition method. In order to manufacture an organic light-emitting display apparatus using the independent deposition method, a fine metal mask (FMM) having the same pattern as an organic layer or the like to be formed is disposed closely contacting a surface of a substrate on which the organic layer will be formed, and an organic material is deposited to form an organic layer having a predetermined pattern.

However, the method using such a fine metal mask (FMM) has a limitation in that it is unsuitable for the manufacturing of a large-sized organic light-emitting display apparatus using a large-sized mother-glass. This is because the use of a large-sized mask may cause a distortion phenomenon of the mask due to the weight of the mask itself to thus generate a pattern distortion. This is contrary to the current trends requiring high definition patterns.

Moreover, since the procedures of aligning and closely contacting the substrate and the fine metal mask, performing a deposition, and separating the fine metal mask from the substrate take much time, the manufacturing time is long and the production yield may be low.

Information disclosed in this Background section was already known to the inventors of the present invention before achieving the present invention or is technical information acquired in the process of achieving the present invention. Therefore, it may contain information that does not form the prior art that is already known to a person of ordinary skill in the art.

SUMMARY

One or more embodiments of the present invention include an apparatus for monitoring deposition rate that is easy to manufacture, may be easily applied to a process for mass production of a large-sized substrate, and enables a high resolution patterning, an apparatus provided with the same, for depositing an organic layer, a method of monitoring deposition rate, and a method of manufacturing an organic light emitting display apparatus using the same.

Additional aspects will be set forth in part in the description which follows and, in part, will be apparent from the description, or may be learned by practice of the presented embodiments.

According to one or more embodiments of the present invention, a deposition rate monitoring apparatus for measuring deposition rate of a deposition material discharged from a deposition source, includes: a light source configured to irradiate light having a wavelength within a photoexcitation bandwidth of the deposition material; a first optical system configured to irradiate the light emitted from the light source toward the discharged deposition material; a second optical system configured to collect the light emitted from the deposition material; and a first light sensor configured to detect an amount of the light which is emitted from the deposition material and collected in the second optical system.

The light source may selectively emit only the light having a wavelength for exciting the deposition material.

The second optical system may detect an amount of fluorescence which is irradiated to the deposition material by the first optical system and is excited.

The first optical system may irradiate the light emitted from the light source toward a deposition source nozzle from which the deposition material is discharged.

The above deposition rate monitoring apparatus may further include a second light sensor for measuring an intensity of the light irradiated from the light source.

A signal detected by the first light sensor and a signal detected by the second light sensor may be normalized.

The above deposition rate monitoring apparatus may further include a third light sensor for detecting lights other than fluorescence among the lights emitted from the deposition material.

A signal detected by the third light sensor may be subtracted from a signal detected by the first light sensor.

The first optical system may include: a lens; a protective window formed at one side of the lens to protect the lens; and a heating member for heating the protective window.

The first optical system may include: a lens; a protective window formed at one side of the lens to protect the lens; and a protective member formed extending from the protective window toward the deposition source.

According to one or more embodiments of the present invention, an organic layer deposition apparatus includes: a conveyor unit including a moving unit configured to attach a substrate thereto and to be movable together with the attached substrate, a first transfer unit configured to transfer the moving unit to which the substrate is attached in a first direction, and a second transfer unit configured to transfer the moving unit, which is separated from the substrate after completion of deposition, in an opposite direction to the first direction; and one or more organic layer deposition assemblies configured to deposit an organic layer on the substrate attached to the moving unit, wherein each of the organic layer deposition assemblies includes: one or more deposition sources configured to discharge a deposition material; a deposition source nozzle part located at one side of the deposition source and including one or more deposition source nozzles; a patterning slit sheet facing the deposition source nozzle part and having a plurality of patterning slits arranged along a direction; and a deposition rate monitoring apparatus described above, and wherein the moving unit is configured to be circulated between the first transfer unit and the second transfer unit, and the substrate attached to the moving unit is spaced apart from the organic layer deposition assemblies while the substrate is transferred by the first transfer unit.

According to one or more embodiments of the present invention, a deposition rate monitoring method for measuring a deposition rate of a deposition material discharged from a deposition source, includes: emitting light having a wavelength within a photoexcitation bandwidth of the deposition material from a light source; irradiating the light emitted from the light source toward the deposition material discharged from the deposition source; and detecting an amount of the light emitted from the deposition material which is excited by the irradiated light.

The emitting of the light from the light source may include selectively emitting only the light having a wavelength for exciting the deposition material from the light source.

The detecting of the light may include detecting an amount of fluorescence emitted from the deposition material which is excited by the irradiated light.

The emitting of the light from the light source may further include measuring an intensity of the light irradiated from the light source.

The above deposition rate monitoring method may further include normalizing a signal detected in the detecting of the amount of the light emitted from the deposition material which is excited by the irradiated light, and a signal detected in the measuring of an intensity of the light irradiated from the light source.

The detecting of the amount of the light emitted from the deposition material which is excited by the irradiated light may further include detecting amounts of lights other than fluorescence among the lights emitted from the deposition material.

The above deposition rate monitoring method may further include subtracting the lights other than the fluorescence among the lights emitted from the deposition material from the light emitted from the deposition material which is excited by the irradiated light.

The above deposition rate monitoring method may further include heating a first optical system which irradiates the light emitted from the light source toward the deposition material discharged from the deposition source.

According to one or more embodiments of the present invention, a method of manufacturing an organic light-emitting display apparatus using an organic layer deposition apparatus to form an organic layer on a substrate, includes: transferring, into a chamber, a moving unit to which the substrate is attached, by using a first transfer unit passing through the chamber; forming the organic layer by depositing a deposition material discharged from an organic layer deposition assembly on the substrate while the substrate is moved relative to the organic layer deposition assembly with the organic layer deposition assembly in the chamber being spaced apart from the substrate; and returning the moving unit separated from the substrate using a second transfer unit passing through the chamber, wherein the forming of the organic layer includes: emitting light having a wavelength within a photoexcitation bandwidth of the deposition material from a light source; irradiating the light emitted from the light source toward the deposition material discharged from the deposition source; and detecting the light emitted from the deposition material which is excited by the irradiated light.

BRIEF DESCRIPTION OF THE DRAWINGS

These and/or other aspects will become apparent and more readily appreciated from the following description of the embodiments, taken in conjunction with the accompanying drawings of which:

FIG. 10 is a schematic view illustrating another embodiment of the deposition rate monitoring apparatus 180, which may be used in the deposition part 100 of FIG. 3.

DETAILED DESCRIPTION

Figure 1:
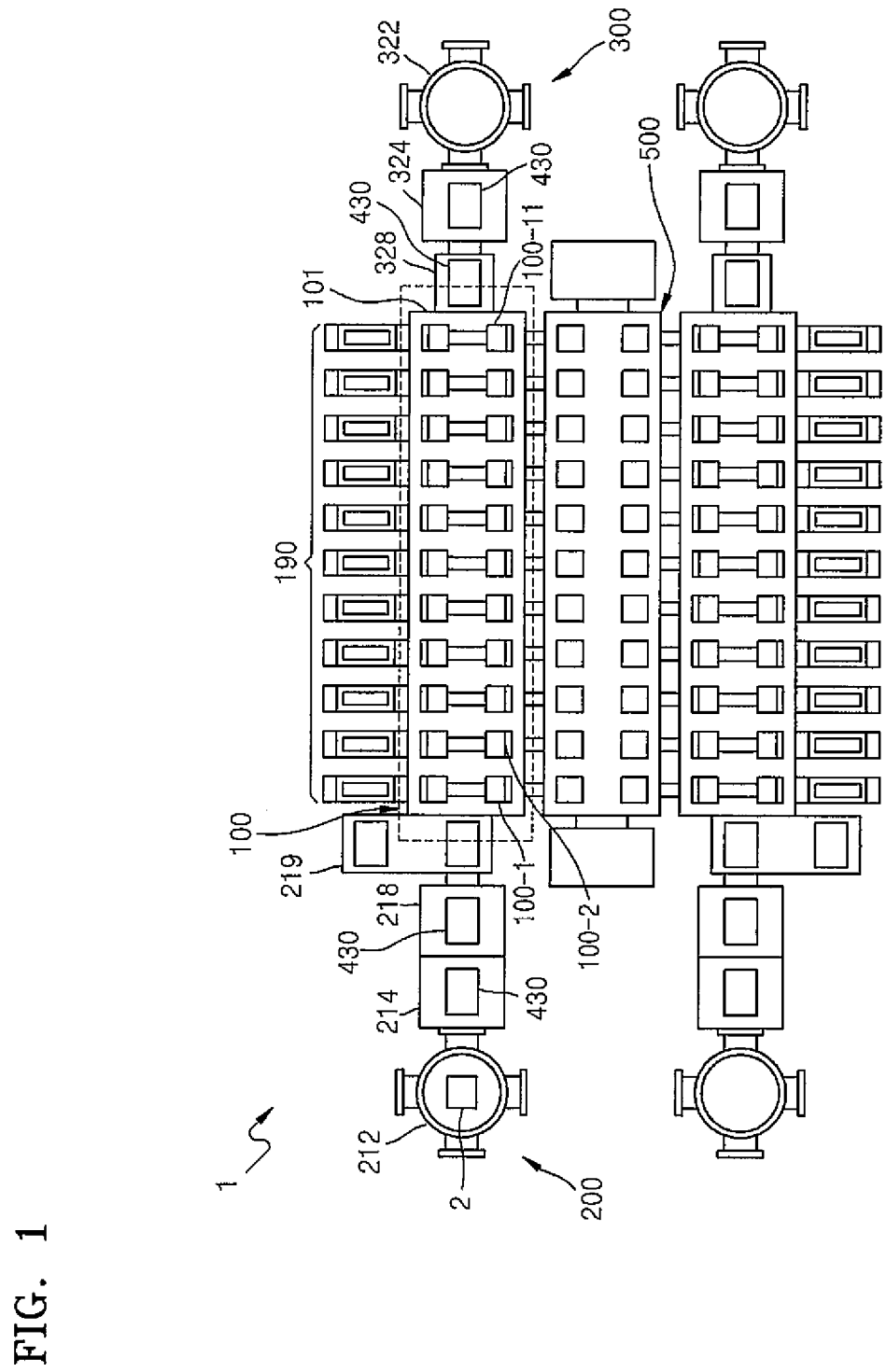
FIG. 1 is a plan view of a system configuration schematically illustrating an apparatus for depositing an organic layer according to an embodiment of the present invention.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

In the following detailed description, reference is made to the accompanying drawings that show, by way of illustration, specific embodiments in which the present invention may be practiced. These embodiments are described in sufficient detail to enable those skilled in the art to practice the present invention. It is to be understood that the various embodiments, although different, are not necessarily mutually exclusive. For example, a particular feature, structure, or characteristic described herein, in connection with one embodiment, may be implemented within other embodiments without departing from the spirit and scope of the present invention. In addition, it is to be understood that the location or arrangement of individual elements within each disclosed embodiment may be modified without departing from the spirit and scope of the claimed subject matter. The following detailed description is, therefore, not to be taken in a limiting sense, and the scope of the present invention is defined by the appended claims, appropriately interpreted, along with the full range of equivalents to which the appended claims are entitled. In the drawings, like numerals refer to the same or similar elements or functionality throughout the several views.

Hereinafter, various embodiments of the present invention will be described in detail with reference to the accompanying drawings so as to enable those skilled in the art to easily practice the present invention.

Figure 2:
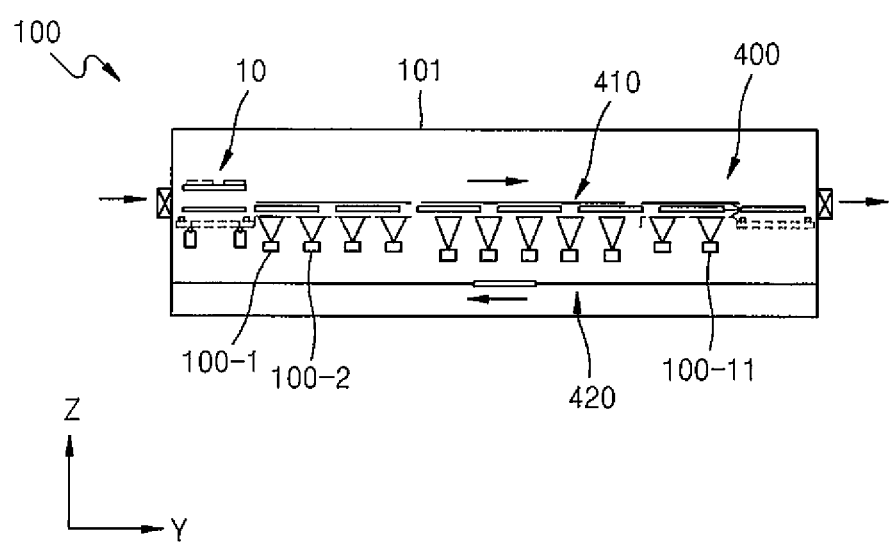
FIG. 2 is a side view of a system configuration schematically illustrating a deposition part of the organic layer deposition apparatus of FIG. 1.

FIG. 1 is a plan view of a system configuration schematically illustrating an apparatus for depositing an organic layer according to an embodiment of the present invention, and FIG. 2 is a side view of a system configuration schematically illustrating a deposition part of the organic layer deposition apparatus of FIG. 1.

Referring to FIGS. 1 and 2, an apparatus 1 for depositing an organic layer according to an embodiment of the present invention includes a deposition part 100, a loading part 200, an unloading part 300, and a conveyer unit 400.

The loading part 200 may include a first rack 212, an introducing room (e.g., a transport chamber or an insertion chamber) 214, a first inverting room (e.g., a first inversion chamber) 218, and a buffer chamber 219.

A plurality of substrates 2 before deposition are stacked on the first rack 212, and an insertion robot (or a transport robot) provided in the insertion chamber 214 holds the substrate 2 from the first rack 212, loads the substrate 2 on a moving unit 430 transferred from a second transfer unit 420, and then moves the moving unit 430 on which the substrate 2 is placed to the first inversion chamber 218.

The first inversion chamber 218 is provided to be adjacent to the insertion chamber 214, and a first inverting robot positioned in the first inversion chamber 218 inverts the moving unit 430 to equip the moving unit 430 in a first transfer unit 410 of the deposition part 100.

As viewed from FIG. 1, the insertion robot of the insertion chamber 214 loads the substrate 2 on a top surface of the moving unit 430, the moving unit 430 moves to the inversion chamber 218, and as the first inverting robot of the inversion chamber 218 inverts the moving unit 430, the substrate 2 in the deposition part 100 is positioned to face the downward direction.

The unloading part 300 has an opposite configuration to the above-described loading part 200. That is, a second inverting robot of a second inversion chamber 328 inverts the substrate 2 and the moving unit 430 that have passed through the deposition part 100, transfers the substrate 2 and the moving unit 430 to an extraction chamber 324, an extraction robot takes out the substrate 2 and the moving unit 430 from the extraction chamber 324, separates the substrate 2 from the moving unit 430, and loads the separated substrate 2 on a second rack 322. The moving unit 430 separated from the substrate 2 returns to the load part 200 through the second transfer unit 420.

However, the present invention is not necessarily limited thereto. For example, the substrate 2 may be fixed (or attached) to a lower surface of the moving unit 430 when being first fixed (or attached) to the moving unit 430 and transferred to the deposition part 100. In this case, the first inverting robot of the first inversion chamber 218 and the second inverting robot of the second inversion chamber 328 are not necessary.

The deposition part 100 includes at least one deposition chamber 101. According to an embodiment shown in FIGS. 1 and 2, the deposition part 100 includes the chamber 101, and a plurality of organic layer deposition assemblies 100-1, 100-2, . . . , and 100-11 are located in the chamber 101. According to an embodiment shown in FIG. 1, while eleven organic layer deposition assemblies, i.e., a first organic layer deposition assembly 100-1, a second organic layer deposition assembly 100-2, . . . , and an eleventh organic layer deposition assembly 100-11 are installed in the chamber 101, the number of the organic layer deposition assemblies may be changed according to the deposition material and deposition condition. The chamber 101 is maintained in vacuum while deposition is performed.

Meanwhile, according to an embodiment of the present invention shown in FIG. 1, the moving unit 430 to which the substrate 2 is fixed (or attached) moves to at least the deposition part 100, and for example, sequentially to the loading part 200, the deposition part 100 and the unloading part 300 by the first transfer unit 410, and the moving unit 430 which is separated from the substrate 2 at the unloading part 300 returns to the loading part 200 by the second transfer unit 420.

The first transfer unit 410 is provided to penetrate the chamber 101 while passing through the deposition part 100, and the second transfer unit 420 is provided to transfer the moving unit 430 separated from the substrate 2.

Since the organic layer deposition apparatus 1 according to an embodiment of the present invention is configured such that the first transfer unit 410 and the second transfer unit 420 are formed at upper and lower sides, respectively, and the moving unit 430 completing a deposition while passing through the first transfer unit 410 is separated from the substrate 2 at the unloading part 300 and returns to the loading part 200 through the second transfer unit 420 formed thereunder, efficiency in use of space may be enhanced.

Meanwhile, the deposition part 100 shown in FIG. 1 may further include a deposition source replacement part 190 at one side of each of the organic layer deposition assemblies 100-1. Although not shown in detail in the drawings, the deposition source replacement part 190 may be formed in a cassette type so as to be withdrawn to an outside from each of the organic layer deposition assemblies 100-1. Therefore, it may be easy to replace a deposition source (see 110 of FIG. 3) of the organic layer deposition assembly 100-1.

Meanwhile, it is shown in FIG. 1 that two sets of organic layer deposition apparatuses each including the loading part 200, the deposition part 100, the unloading part 300, and the conveyor unit 400 are provided. That is, it may be understood that in total two organic layer deposition apparatuses 1 are provided at an upper side and a lower side (for example, in parallel or side-by-side) as can be seen in FIG. 1. In this case, a patterning slit sheet replacement part 500 may be further provided between the two organic layer deposition apparatuses 1. In other words, since the patterning slit sheet replacement part 500 is provided between the two organic layer deposition apparatuses 1 to allow the two organic layer deposition apparatuses 1 to share the patterning slit sheet replacement part 500, efficiency in use of space may be enhanced, compared with a case in which each of the organic layer deposition apparatuses has its own patterning slit sheet replacement part 500.

Figure 3:
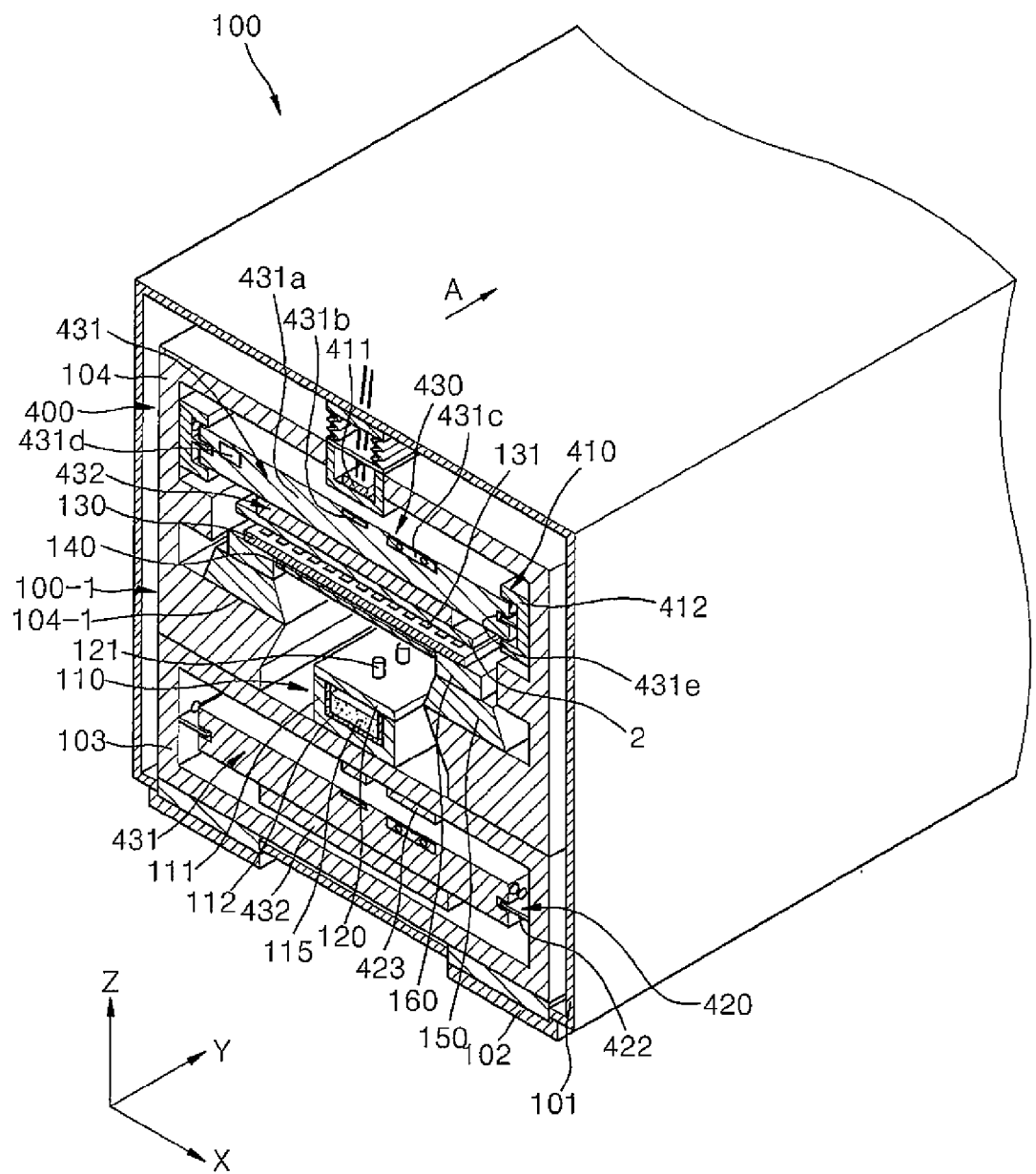
FIG. 3 is a perspective view schematically illustrating the deposition part of FIG. 1.
Figure 4:
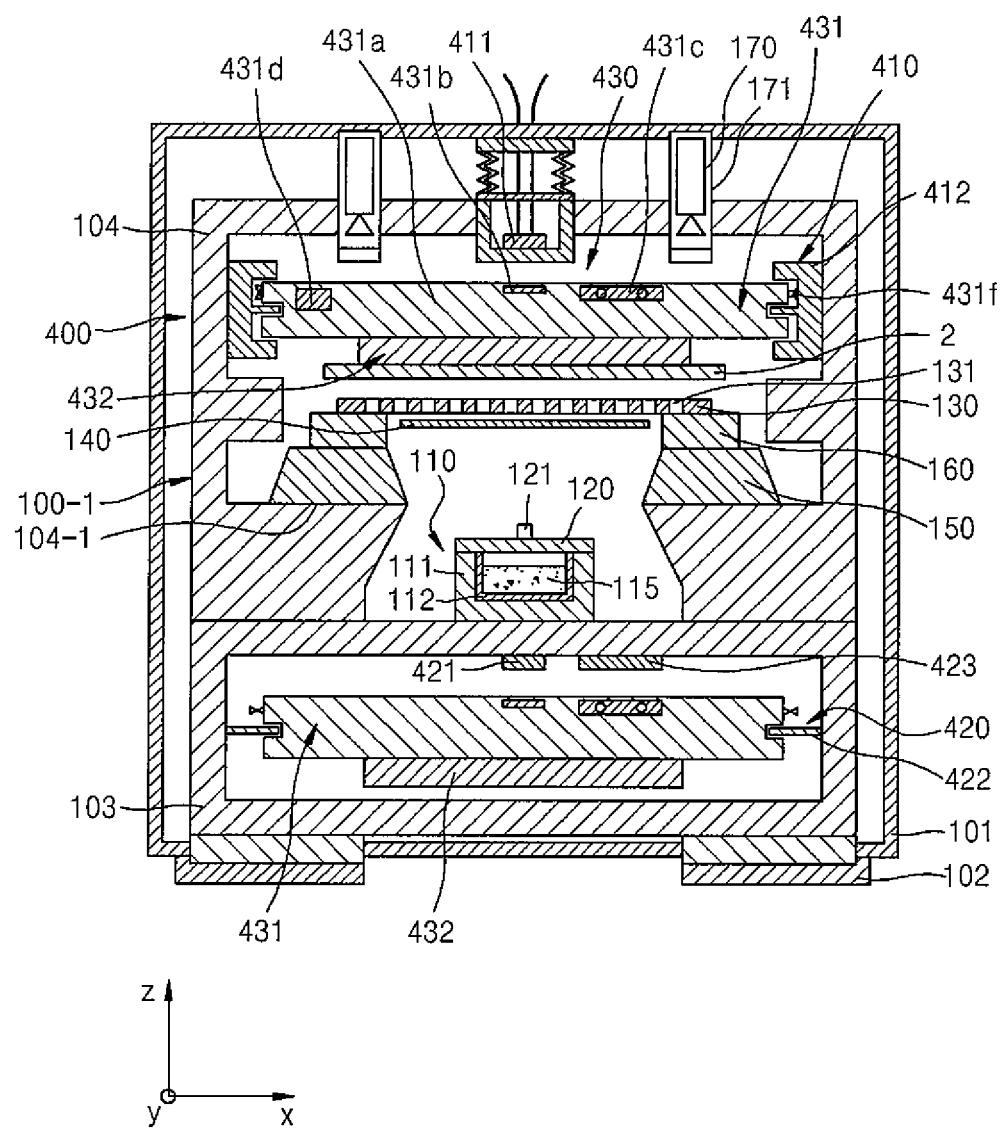
FIG. 4 is a schematic cross-sectional view of the deposition part of FIG. 3.

FIG. 3 is a perspective view schematically illustrating the deposition part of FIG. 1, and FIG. 4 is a schematic cross-sectional view of the deposition part of FIG. 3.

First, referring to FIGS. 3 and 4, the deposition part 100 of the organic layer deposition apparatus 1 according to an embodiment of the present invention includes at least one organic layer deposition assembly 100-1, and the conveyor unit 400.

Hereinafter, the overall configuration of the deposition part 100 will be described.

The chamber 101 has a hollow box shape, and receives (or accommodates) at least one organic layer deposition assembly 100-1 and the conveyor unit 400 therein. As described in another aspect, a foot 102 is formed such that the chamber is fixed to the ground, a lower housing 103 is located on the foot 102, and an upper housing 104 is located on the lower housing 103. The chamber 101 is configured to receive both of the lower housing 103 and the upper housing 104 therein. A connecting part between the lower housing 103 and the chamber 101 is sealed such that an inside of the chamber 101 may be completely shielded from an outside. Thus, since the lower housing 103 and the upper housing 104 are located on the foot 102 fixed to the ground, the lower housing 103 and the upper housing 104 may maintain fixed positions while the chamber 101 repeats contraction/expansion, and thus the lower housing 103 and the upper housing 104 function as a reference frame within the deposition part 100.

Meanwhile, the organic layer deposition assembly 100-1 and the first transfer unit 410 of the conveyor unit 400 are located inside the upper housing 104, and the second transfer unit 420 of the conveyor unit 400 is located inside the lower housing 103. While the moving unit 430 moves repeatedly between the first transfer unit 410 and the second transfer unit 420, successive deposition is performed.

Hereinafter, the configuration of the organic layer deposition assembly 100-1 will be described in detail.

Each of the organic layer deposition assemblies 100-1 includes a deposition source 110, a deposition source nozzle part 120, a patterning slit sheet 130, a shielding member 140, a first stage 150, and a second stage 160. The deposition part 100 of embodiments according to the present invention may further include a deposition monitoring apparatus (for example, see 180 of FIG. 5) for measuring deposition rate of a deposition material discharged from the deposition source 110. The deposition rate monitoring apparatus 180 will be described in more detail later with reference to FIG. 5.

In example embodiments, all the elements shown in FIGS. 3 and 4 are located in the chamber 101 that maintains a proper vacuum. This is to secure linearity of the deposition material.

A substrate 2 on which the deposition material is deposited is placed in (e.g., inserted into) the chamber 101. The substrate 2 may be a substrate for flat panel display apparatuses, for example, a large-sized substrate having a size of 40 inches or more, such as a mother glass that can be used to form a plurality of flat panel display apparatuses.

Embodiments of the present invention are characterized in that a deposition for the substrate 2 is performed while the substrate 2 moves relative to the organic layer deposition assembly 100-1.

In detail, in a conventional fine metal mask (FMM) deposition method, the size of the FMM be equal to that of the substrate. Therefore, the increase in size of the substrate requires the increase in size of the FMM, and thus it is not easy to manufacture the FMM and it is also not easy to engrave and align fine patterns on the FMM.

To solve such limitations, the organic layer deposition assembly 100-1 according to embodiments of the present invention is characterized in that a deposition is performed while the organic layer deposition assembly 100-1 and the substrate 2 move relative to each other. In other words, successive depositions are performed while the substrate 2 facing the organic layer deposition assembly 100-1 moves along the Y-axis direction. That is, the deposition is performed in a scanning manner while the substrate 2 moves in the direction of an arrow A of FIG. 3. Although it is shown that the deposition is performed while the substrate 2 moves in the Y-axis direction within the chamber (not shown), the spirit and scope of the present invention is not limited thereto. The deposition may be performed while the substrate 2 is fixed in location and the organic layer deposition assembly 100-1 moves in the Y-axis direction with respect to the substrate 2.

Accordingly, the patterning slit sheet 130 may be made smaller in the organic layer deposition assembly 100-1 according to embodiments of the present invention than in the existing FMM. That is, in the case of the organic layer deposition assembly 100-1 according to embodiments of the present invention, since the deposition is successively performed in a scanning manner while the substrate 2 moves in the Y-axis direction, the length of the patterning slit sheet 130 in at least one of the X-axis direction or the Y-axis direction may be formed smaller (e.g., much smaller) than the respective width or length of the substrate 2. Thus, since the patterning slit sheet 130 may be made smaller (e.g., much smaller) than the existing FMM, the patterning slit sheet 130 according to embodiments of the present invention may be easily manufactured. That is, in all processes including an etching, a fine engraving and welding, and a moving and cleaning of the patterning slit sheet 130, the patterning slit sheet 130 having a smaller size is advantageous compared with the FMM deposition method. Also, this is more advantageous as the size of a display apparatus increases.

Thus, in order to perform a deposition while the organic layer deposition assembly 100-1 and the substrate 2 move relative to each other, it is desirable that the organic layer deposition assembly 100-1 is spaced apart (e.g., spaced apart by a predetermined distance) from the substrate 2. This matter will be described in detail later.

Meanwhile, the deposition source 110 in which the deposition material 115 is received and heated is located at a side facing the substrate 2 within the chamber. As the deposition material 115 received in the deposition source 110 is evaporated, deposition is performed on the substrate 2.

In detail, the deposition source 110 includes a crucible 111 with which the deposition material 115 is filled therein, and a heater 112 for heating the crucible 111 to evaporate the deposition material 115 filled in the crucible 111 toward one side of the crucible 111, in more detail, toward the deposition source nozzle part 120.

The deposition source nozzle part 120 is located at one side of the deposition source 110, in detail, at a side facing the substrate 2. In the organic layer deposition assembly according to embodiments of the present invention, the deposition source nozzle for depositing a common layer may be different from the deposition source nozzle for depositing a pattern layer.

The patterning slit sheet 130 is provided between the deposition source 110 and the substrate 2. The patterning slit sheet 130 further includes a frame having a window frame shape, and a plurality of patterning slits 131 formed (or arranged) along the X-axis direction. The deposition material 115 which is evaporated from the deposition source 110 passes through the deposition source nozzle part 120 and the patterning slit sheet 130 and is directed toward the substrate 2 that is a deposition object (or a deposition target). At this time, the patterning slit sheet 130 may be manufactured through an etching that is the same as a process for manufacturing the existing fine metal mask (FMM), especially, a stripe type mask. In this regard, the total number of the patterning slits 131 may be more than the total number of the deposition source nozzles 121. In the embodiment illustrated in FIGS. 3 and 4, the source nozzles 121 are arranged along the Y-axis as a single row or column. In other embodiments, the source nozzles may be arranged along the X-axis. Also in still other embodiments, the source nozzles may be arranged along the Y-axis, but may be arranged to form two or more rows or columns.

The above-mentioned deposition source 110 (and the deposition nozzle part 120 coupled thereto), and the patterning slit sheet 130 may be spaced apart (e.g., spaced apart by a predetermined distance) from each other.

As described above, the deposition is performed while the organic layer deposition assembly 100-1 moves relative to the substrate 2, and the patterning slit sheet 130 is spaced apart (e.g., spaced apart by a predetermined distance) from the substrate 2 such that the organic layer deposition assembly 100-1 moves relative to the substrate 2.

In detail, in the existing FMM deposition method, deposition is performed in a state that the mask is closely contacted with the substrate in order to prevent a shadow from being generated. However, in the case the mask is closely contacted with the substrate as in the existing FMM deposition method, a failure may be generated due to contact between the substrate and the mask. Also, since it fails to move the mask with respect to the substrate, the mask and the substrate should have the same size. According to the FMM deposition method, while the increase in size of the display apparatus requires the increase in size of the mask, it is not easy to form a large-sized mask.

To solve such limitations, in the organic layer deposition assembly 100-1 according to embodiments of the present invention, the patterning slit sheet 130 is positioned spaced apart (e.g., spaced apart by a predetermined distance) from the substrate 2, which is a deposition object (or a deposition target).

According to embodiments of the present invention, since the mask is formed smaller than the substrate, and deposition may be performed while the mask moves with respect to the substrate, it is easy or relatively easy to manufacture the mask. Also, a failure due to contact between the substrate and the mask may be prevented. Further, since the time taken in closely contacting the substrate and the mask in a process is not required, the manufacturing speed may be enhanced.

Next, a concrete arrangement of respective elements in the upper housing 104 will be described.

First, the deposition source 110 and the deposition source nozzle part 120 are located at a bottom of the upper housing 104. Mounting parts 104-1 are formed protruding at both sides of the deposition source 110 and the deposition source nozzle part 120, and a first stage 150, a second stage 160, and the patterning slit sheet 130 are sequentially located on the mounting parts 104-1.

The first stage 150 is formed so as to be movable in the Y-axis direction and the X-axis direction and functions to align the patterning slit sheet 130 in the X-axis direction and the Y-axis direction. That is, the first stage 150 is provided with a plurality of actuators to move in the X-axis direction and the Y-axis direction.

Meanwhile, the second stage 160 is formed to be movable in a Z-axis direction and functions to align the patterning slit sheet 130 in the Z-axis direction. That is, the second stage 160 is provided with a plurality of actuators to move in the Z-axis direction with respect to the first stage 150.

Meanwhile, the patterning slit sheet 130 is located on the second stage 160. Thus, since the patterning slit sheet 130 is located on the first stage 150 and the second stage 160 to be movable in the X-axis direction, the Y-axis direction and the Z-axis direction, the alignment between the substrate 2 and the patterning slit sheet 130 may be performed.

Further, the upper housing 104, the first stage 150 and the second stage 160 may also function to guide a moving path of a deposition material such that the deposition material discharged through the deposition source nozzle 121 is not dispersed. That is, the upper housing 104, the first stage 150, and the second stage 160 may guide the movement of the deposition material in the X-axis direction and the Y-axis direction at the same time by closing the moving path of the deposition material.

Meanwhile, the shielding member 140 may be further provided between the patterning slit sheet 130 and the deposition source 110. The shielding member 140 may function to shield the deposition material 115 discharged from the deposition source 110.

Hereinafter, the conveyor unit 400 for transferring the deposition object (or the deposition target), i.e., the substrate 2 will be described in detail. Referring to FIGS. 3 and 4, the conveyor unit 400 includes the first transfer unit 410, the second transfer unit 420, and the moving unit 430.

The first transfer unit 410 functions to transfer the moving unit 430 including a carrier 431 and an electro static chuck 432 coupled to the carrier 431, and the substrate 2 attached on the moving unit 430, in in-line such that an organic layer may be deposited on the substrate 2 by the organic layer deposition assembly 100-1.

The second transfer unit 420 functions to return the moving unit 430 that has completed one time deposition and is separated from the substrate 2 at the unloading part 300, to the loading part 200. The second transfer unit 420 includes a coil 421, a roller guide 422, and a charging track 423.

The moving unit 430 includes the carrier 431 moving along the first transfer unit 410 and the second transfer unit 420, and the electro static chuck 432 coupled to one surface of the carrier 431, and on which the substrate 2 is attached.

Hereinafter, respective elements constituting the conveyor unit 400 will be described in more detail.

First, the carrier 431 of the moving unit 430 will be described in more detail.

The carrier 431 includes a main body 431a, a linear motion system (LMS) magnet (e.g., a magnetic rail) 431b, a contactless power supply (CPS) module 431c, a power supply 431d, and a guide groove 431e. The carrier 431f may also include cam followers 431f as shown in FIG. 4.

The main body 431a constitutes a bottom portion of the carrier 431 and may be formed of a magnetic material, such as iron. The carrier 431 may maintain a state spaced apart (e.g., spaced apart by a predetermined distance) from the guide part 412 by a magnetic force between the main body 431a of the carrier 431 and a magnetic levitation bearing (not shown).

The guide groove 431e may be formed at both sides of the main body 431a, and a guide protrusion of the guide part 412 may be received in the guide groove 431e.

The magnetic rail 431b may be formed along a center line of the main body 431a in the progressing direction of the main body 431a. The magnetic rail 431b of the main body 431a may be coupled to a coil 411 to be described later to constitute a linear motor, and the carrier 431 may be transferred in the A-direction shown in FIG. 3 by the linear motor.

The CPS module 431c and the power supply 431d may be formed at opposite sides of the magnetic rail 431b in the main body 431a. In one embodiment, the power supply 431d may be a charging battery for providing power to the electro static chuck 432 such that the electro static chuck 432 may chuck (or hold) and maintain the substrate 2, and the CPS module 431c may be a wireless charging module for charging the power supply 431d. The charging track 423 formed in the second transfer unit 420 to be described in detail later is coupled (e.g., connected) to an inverter (not shown) such that power is supplied to the CPS module 431c due to a magnetic field formed between the charging track 423 and the CPS module 431*c* while the carrier 431 is transferred within the second transfer unit 420. The power supplied to the CPS module 431*c* charges the power supply 431*d*.

Meanwhile, the electro static chuck 432 is configured to include a main body formed of ceramics, and an electrode buried in the main body and to which power is applied, and allows the substrate 2 to be mounted on (e.g., attached to) a surface of the main body when a high voltage is applied to the electrode.

Next, operations of the moving unit 430 will be described in detail.

The magnetic rail 431*b* of the main body 431*a* and the coil 411 may be coupled to each other to constitute a driving part. The driving part may be a linear motor. The linear motor has a smaller friction coefficient than an existing sliding guidance system and has a high positioning accuracy (e.g., a very high positioning accuracy) since it generates little or substantially no position error. As described above, the linear motor may include the coil 411 and the magnetic rail 431*b*, in which the magnetic rail 431*b* is arranged in a line on the carrier 431, and the plurality of coils may be located (e.g., located at a predetermined interval) at one side within the chamber 101 so as to face the magnetic rail 431*b*. Thus, since the magnetic rail 431*b* instead of the coil 411 is located in the carrier 431 that is a moving object, the carrier 431 may be driven although power is not applied thereto. In example embodiments, the coil 411 is formed in an atmosphere (ATM) box and installed in an atmospheric state, and the magnetic rail 431*b* is attached to the carrier 431 such that the carrier 431 travels in the chamber 101 in vacuum.

Meanwhile, the organic layer deposition assembly 100-1 of the organic layer deposition apparatus according to an embodiment of the present invention may be further provided with a camera (or cameras) 170 for alignment. In detail, the camera (or cameras) 170 may align a mark formed on the pattern slit sheet 130 with a mark formed on the substrate 2 in real time. The camera (or cameras) 170 is provided so as to secure a smooth view within the vacuum chamber 101 in which deposition is in progress. For this, the camera (or cameras) 170 may be located in a camera receiving part 171 and installed in the atmospheric state.

Hereinafter, a deposition rate monitoring apparatus 180 of the organic layer deposition apparatus 1 according to an embodiment of the present invention will be described in more detail.

Figure 5:
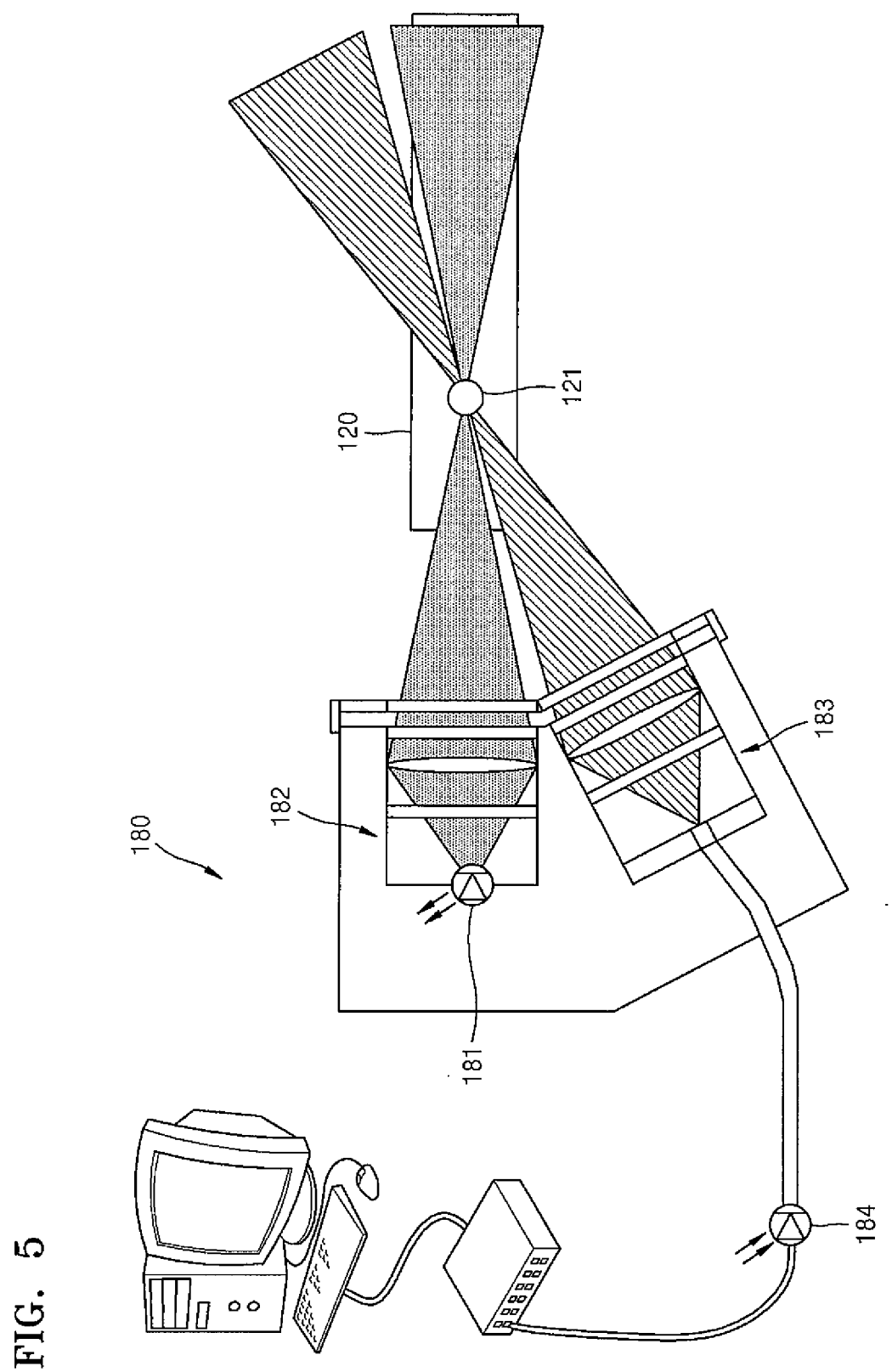
FIG. 5 is a schematic view illustrating an embodiment of a deposition rate monitoring apparatus 180, which may be used in the deposition part 100 of FIG. 3.

FIG. 5 is a schematic view illustrating an embodiment of the deposition rate monitoring apparatus 180, which may be used in and with the deposition unit 100 of FIG. 3.

Referring to FIG. 5, the deposition rate monitoring apparatus 180 includes a light source 181, a first optical system 182, a second optical system 183, and a first light sensor 184. The deposition rate monitoring apparatus 180 of the organic layer deposition apparatus 1 according to an embodiment of the present invention is characterized by monitoring the deposition rate of the deposition material (see for example, the deposition material 115 of FIG. 3) that is a fluorescent material, using a fluorescence measuring method at one side of the deposition source (see for example, the deposition source 110 of FIG. 3) and the deposition source nozzle part 120.

For example, the properties of an organic light-emitting apparatus considerably depend on the thickness of a deposited organic material. Therefore, according to embodiments of the present invention, in order to manufacture an organic light-emitting display apparatus having superior quality, a work of measuring the deposition rate of the deposition material and correcting the measured deposition rate is used. An existing method of monitoring the deposition rate of a deposition material includes depositing an organic material on a substrate on which an organic material is not deposited, at a constant deposition rate, measuring the thickness of the organic material deposited on the substrate using an analysis tool, such as an ellipsometer capable of measuring the thickness of a deposited material, changing a tooling factor (T/F) of the organic material or adjusting the deposition rate using the measured thickness to deposit the organic material at a desired target thickness.

When the organic material deposited on the substrate is monitored using such an existing method, the measurement of the deposition rate of the organic material may be affected (e.g., seriously affected) by the inner temperature of the organic layer deposition apparatus. For example, when the inner temperature of the organic layer deposition apparatus rises 10%, an error indicated as the deposition rate measured by the deposition rate monitoring apparatus rising 100% may be generated.

To solve such limitations, the deposition rate monitoring apparatus 180 of the organic layer deposition apparatus according to an embodiment of the present invention is characterized by monitoring the deposition rate of the deposition material (see for example, the deposition material 115 of FIG. 3) that is a fluorescent material, using a fluorescence measuring method, to thus implement a monitoring system that is not affected (or substantially not affected) by temperature, and detailed description of such features will be made hereinbelow.

Again referring to FIG. 5, the deposition rate monitoring apparatus 180 includes the light source 181, the first optical system 182, the second optical system 183, and the first light sensor 184.

The light source 181 irradiates light having a wavelength within a photoexcitation bandwidth of the deposition material (see for example, the deposition material 115 of FIG. 3). While the light source 181 may be a broadband light source, the wavelength of light irradiated from the light source 181 should be within the photoexcitation bandwidth of the deposition material. The irradiation band of the light source 181 may be limited by an optical filter.

The first optical system 182 may include excitation light delivery optics. The first optical system 182 may function to collect light irradiated from the light source within a testing volume of one side of the deposition source nozzle 121 on which the deposition material is concentrated. The first optical system 182 may include a projection lens, and an optical fiber or an optical window of the vacuum chamber. For more efficient photoexcitation of the deposition material, in example embodiments, the first optical system 182 concentrates light in a small volume.

As shown in FIG. 5, light irradiated from the light source 181 is concentrated by the first optical system 182 on the deposition source nozzle 121 of the deposition source nozzle part 120 where the deposition material (see for example, the deposition material 115 of FIG. 3) is concentratively distributed.

The second optical system 183 functions to collect light irradiated from the testing volume and concentrate the collected light on the first light sensor 184. At this time, light transmission may be assisted by an optical fiber.

The first light sensor 184 functions to detect the amount of fluorescence irradiated from the excited deposition material.

A method of measuring the deposition rate of a deposition material using the deposition rate monitoring apparatus 180 of the organic layer deposition apparatus 1 according to an embodiment of the present invention will now be described.

The deposition rate monitoring apparatus 180 collects light irradiated from the light source 181 around the deposition source nozzle 121 of the deposition source nozzle part 120 where the deposition material (see for example, the deposition material 115 of FIG. 3) is concentratively distributed, through the first optical system 182. Meanwhile, most of organic materials used in OLEDs have high fluorescence under UV light excitation. Therefore, in example embodiments, the light source 181 strongly irradiates UV spectrum light. As such a light source, there may be used a typical UV lamp or an LED which is developed in these days.

Meanwhile, light irradiated from the light source 181 is concentrated around the deposition source nozzle 121 of the deposition source nozzle part 120 where the deposition material (see for example, the deposition material 115 of FIG. 3) is concentratively distributed, by the projection lens (e.g., a focusing lens) of the first optical system 182. Light transmission within the vacuum chamber (see 101 of FIG. 3) may be assisted by an optical fiber.

The flow of molecules constituting the deposition material (see for example, the deposition material 115 of FIG. 3) may allow light (fluorescence) to be irradiated by UV light excitation. The amount of irradiated fluorescence is proportional to concentration of molecules within the excited volume, efficiency of fluorescence (depending on (e.g., only on) internal characteristics of the deposition material), and intensity of excitation light. At this time, while dependency of excitation light on the intensity may be non-linear under a very strong light intensity that may be accomplished by (e.g., only by) a high power pulse laser, according to embodiments of the present invention, a low power light source is used.

Since the deposition rate is proportional to a product of concentration of molecules and flow rate of the molecules, the amount of fluorescence may be expressed by the following equation 1.

$$I_{fluorescence} \sim \frac{R_{depositionrate}}{\sqrt{kT}} \qquad \text{Equation 1}$$

where T is temperature of the deposition material.

Then, in most cases, since the temperature of the deposition source (see 110 of FIG. 3) is not greatly changed, Equation 1 may be simplified as Equation 2.

$$I_{fluroescence} \sim \frac{R_{depositionrate}}{\sqrt{kT}} \sim R_{depositionrate} \qquad \text{Equation 2}$$

For example, since the temperature rise of 10° C. causes only a variation of 0.8% in flow rate of molecules, the above-mentioned simplicity (e.g., approximation) is reasonable.

Meanwhile, the light irradiated from the deposition material is collected by the second optical system 183 and is concentrated on the first light sensor 184. At this time, as shown in FIG. 5, the light irradiated from the deposition material may be concentrated on the optical fiber coupled (e.g., connected) to the first light sensor 184. In this regard, since the wavelength of fluorescence is different from that of the excitation light (i.e., the wavelength of fluorescence is shorter than that of the excitation light), it is possible to separate excitation light from the emitted fluorescence.

According to embodiments of the present invention, a monitoring system which is not affected by temperature may be realized by monitoring the deposition rate of the deposition material (see for example, the deposition material 115 of FIG. 3) that is a fluorescent material, using a fluorescence measuring method.

Hereinafter, a deposition rate monitoring apparatus 180*a* of the organic layer deposition apparatus 1 according to another embodiment of the present invention will be described in more detail.

Figure 6:
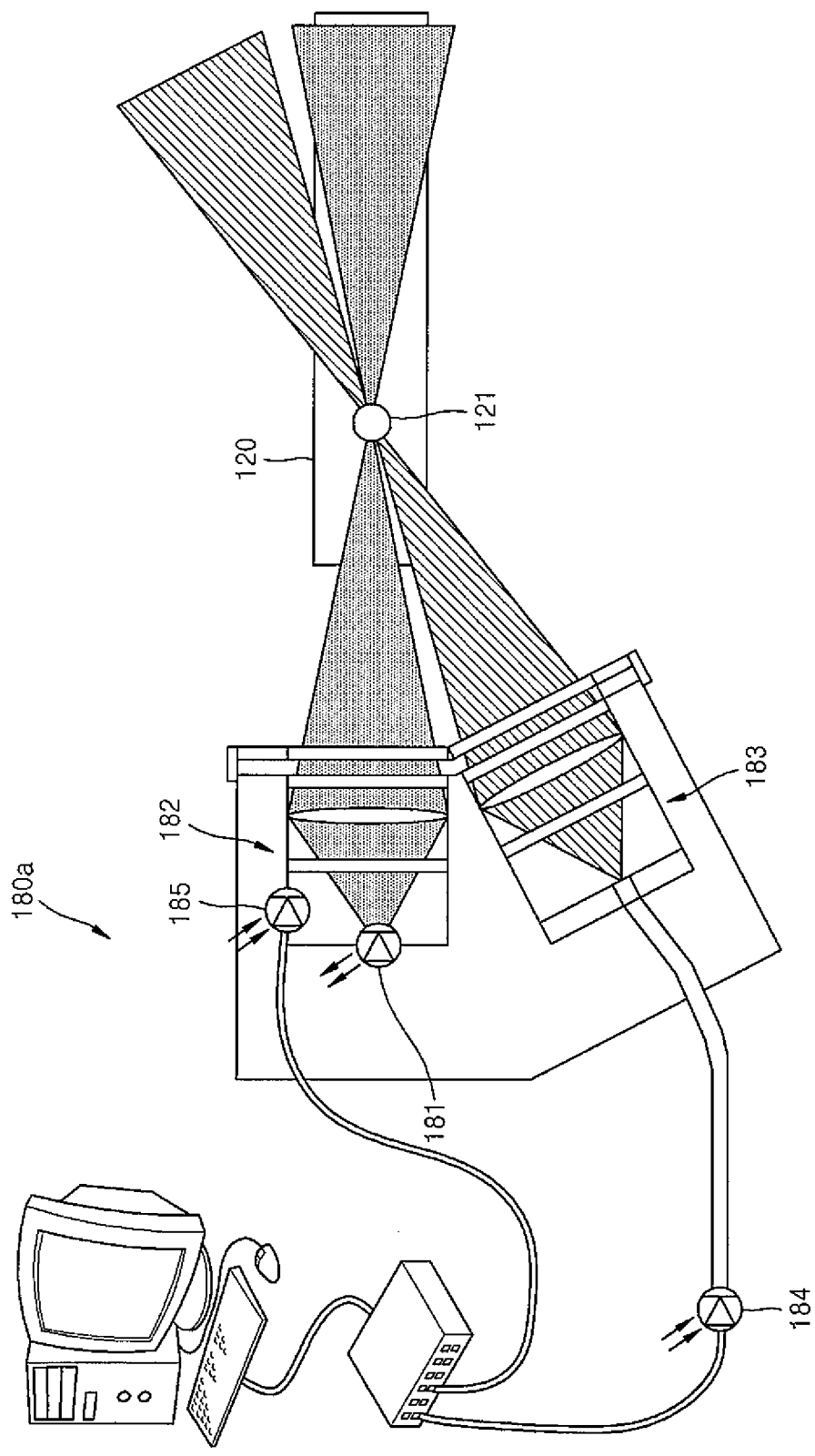
FIG. 6 is a schematic view illustrating another embodiment of the deposition rate monitoring apparatus 180, which may be used in the deposition part 100 of FIG. 3.

FIG. 6 is a schematic view illustrating another embodiment of the deposition rate monitoring apparatus 180*a*, which may be used in and with the deposition unit 100 of FIG. 3. Referring to FIG. 6, the deposition rate monitoring apparatus 180*a* includes a light source 181, a first optical system 182, a second optical system 183, and a first light sensor 184. Compared with the deposition rate monitoring apparatus in the previous embodiment shown in FIG. 5, the deposition rate monitoring apparatus 180*a* according to another embodiment of the present invention is characterized by further including a second light sensor 185.

The second light sensor 185 plays a role as an additional light sensor for measuring the intensity of light irradiated from the light source 181 and at the same time may transmit the measured intensity of light to a controller (e.g., a computer). Therefore, in this embodiment, it is possible to compensate for a change in intensity of light or a decrease in output of the light source by normalizing a signal received by the first light sensor 184 and a signal received by the second light sensor 185.

Hereinafter, a deposition rate monitoring apparatus 180*b* of the organic layer deposition apparatus 1 according to another embodiment of the present invention will be described in more detail.

Figure 7:
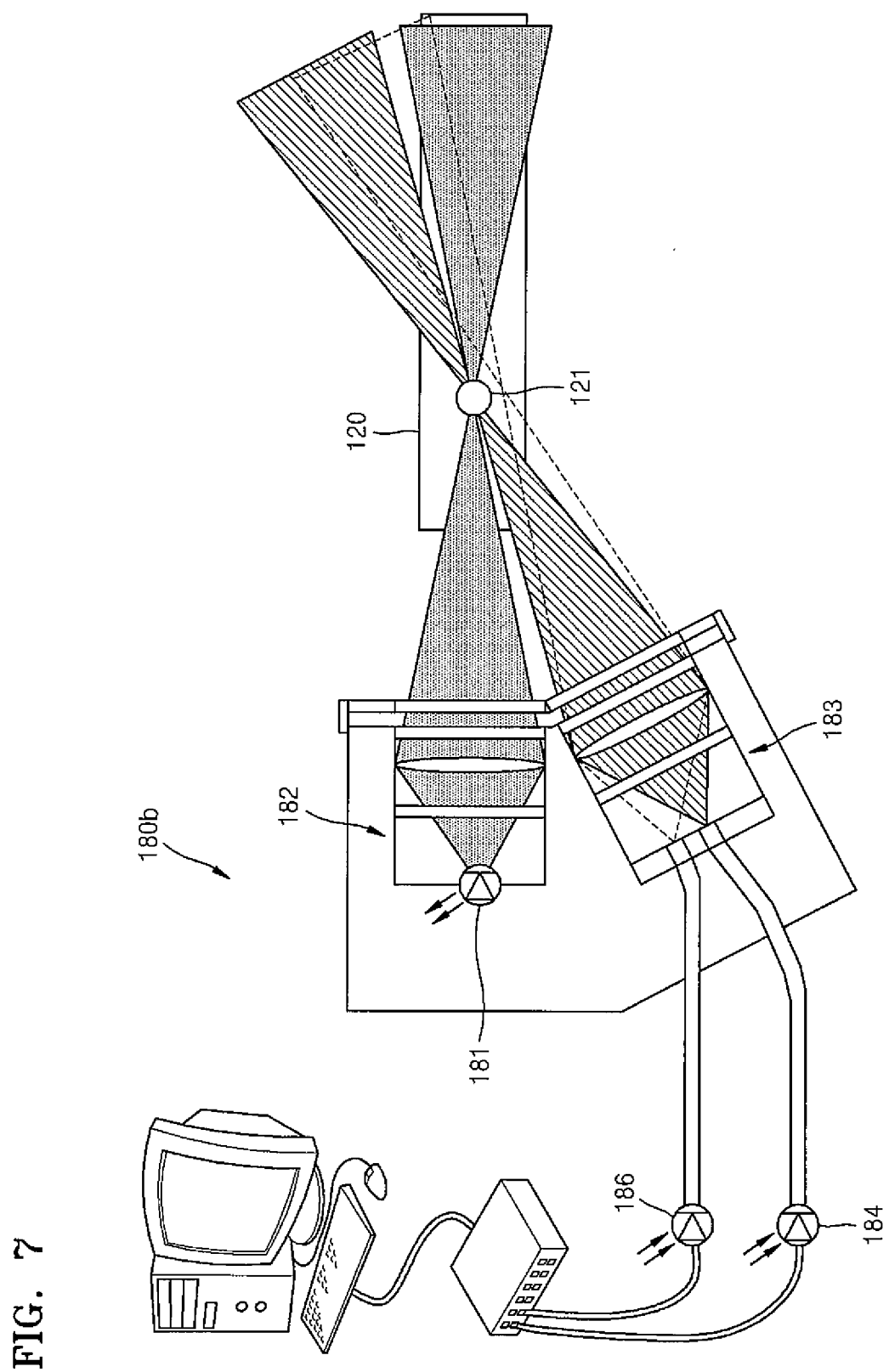
FIG. 7 is a schematic view illustrating another embodiment of the deposition rate monitoring apparatus 180, which may be used in the deposition part 100 of FIG. 3.

FIG. 7 is a schematic view illustrating another embodiment of the deposition rate monitoring apparatus 180*b*, which may be used in and with the deposition unit 100 of FIG. 3. Referring to FIG. 7, the deposition rate monitoring apparatus 180*b* includes a light source 181, a first optical system 182, a second optical system 183, and a first light sensor 184. Compared with the deposition rate monitoring apparatus in the previous embodiment shown in FIG. 5, the deposition rate monitoring apparatus 180*b* according to the present embodiment is characterized by further including a third light sensor 186.

The third light sensor 186 may play a role as an additional light sensor for detecting lights other than the fluorescence emitted from the deposition material. Therefore, in order to detect a pure signal for only the fluorescence emitted from the deposition material, it is necessary to subtract a signal detected by the third light sensor 186 from a signal detected by the first light sensor 184. This is because the first light sensor 184 may detect other lights as well as the fluorescence emitted from the deposition material.

Hereinafter, a deposition rate monitoring apparatus 180*c* of the organic layer deposition apparatus 1 according to another embodiment of the present invention will be described in more detail.

Figure 8:
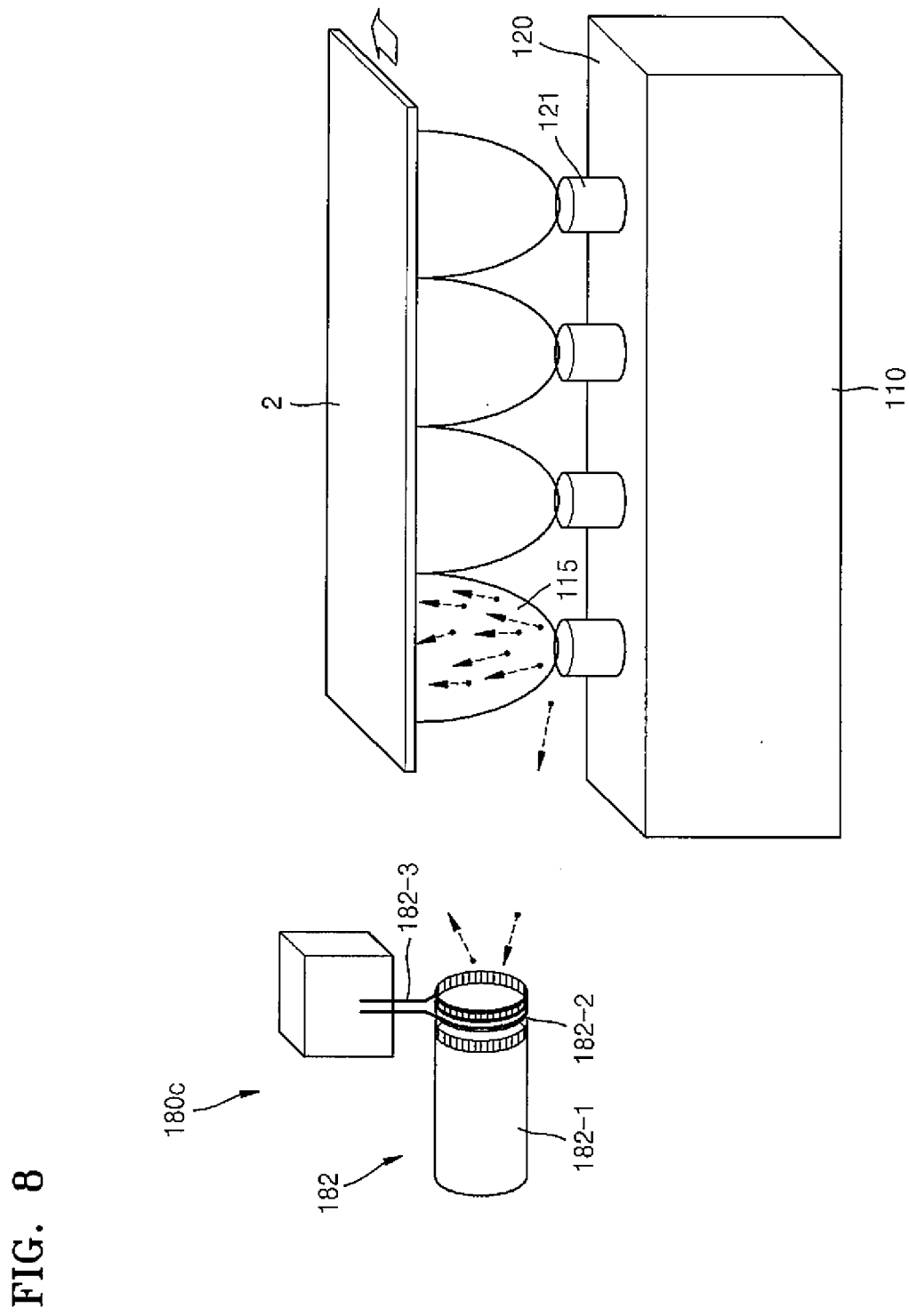
FIG. 8 is a schematic view illustrating another embodiment of the deposition rate monitoring apparatus 180, which may be used in the deposition part 100 of FIG. 3.

FIG. 8 is a schematic view illustrating another embodiment of the deposition rate monitoring apparatus 180*c*, which may be used in and with the deposition unit 100 of FIG. 3. Referring to FIG. 8, the deposition rate monitoring apparatus 180*c* according to the present embodiment includes a light source (see for example, 181 of FIG. 5), a first optical system (see for example, 182 of FIG. 5), a second optical system (see for example, 183 of FIG. 5), and a first light sensor (see for example, 184 of FIG. 5). The first optical system (see for example, 182 of FIG. 5) may include a lens 182-1, and a protective window 182-2, and the protective window 182-2 may be formed with a heating member 182-3.

In detail, as the measurement of the deposition rate of the deposition material progresses, the deposition material may be slowly deposited in the first optical system (see for example, 182 of FIG. 5) to cause limitations (e.g., serious limitations). That is, in the case the deposition material is deposited in the first optical (see for example, 182 of FIG. 5), the first optical system may hinder transmission of light emitted from the first optical system and has an influence on the wavelength of emitted light, and these behaviors may be more serious under a high deposition rate.

To solve such limitations, compared with the deposition rate monitoring apparatus in the previous embodiment shown in FIG. 5, the deposition rate monitoring apparatus 180c according to the present embodiment is characterized by further including the heating member 182-3. That is, the heating member 182-3 is formed at one side of the protective window 182-2 of the first optical system (see for example, 182 of FIG. 5) to heat the protective window 182-2 to a temperature above the sublimation temperature of the deposition material so that the deposition material deposited on the protective window 182-2 is sublimated and delaminated to prevent the deposition material from being deposited on the first optical system (see for example, 182 of FIG. 5).

A nichrome wire or the like may be used as the heating member 182-3, and is heated when current flows therethrough. For this, the protective window 182-2 may be formed of a high thermal conductivity material.

Hereinafter, a deposition rate monitoring apparatus 180d of the organic layer deposition apparatus 1 according to another embodiment of the present invention will be described in more detail.

Figure 9:
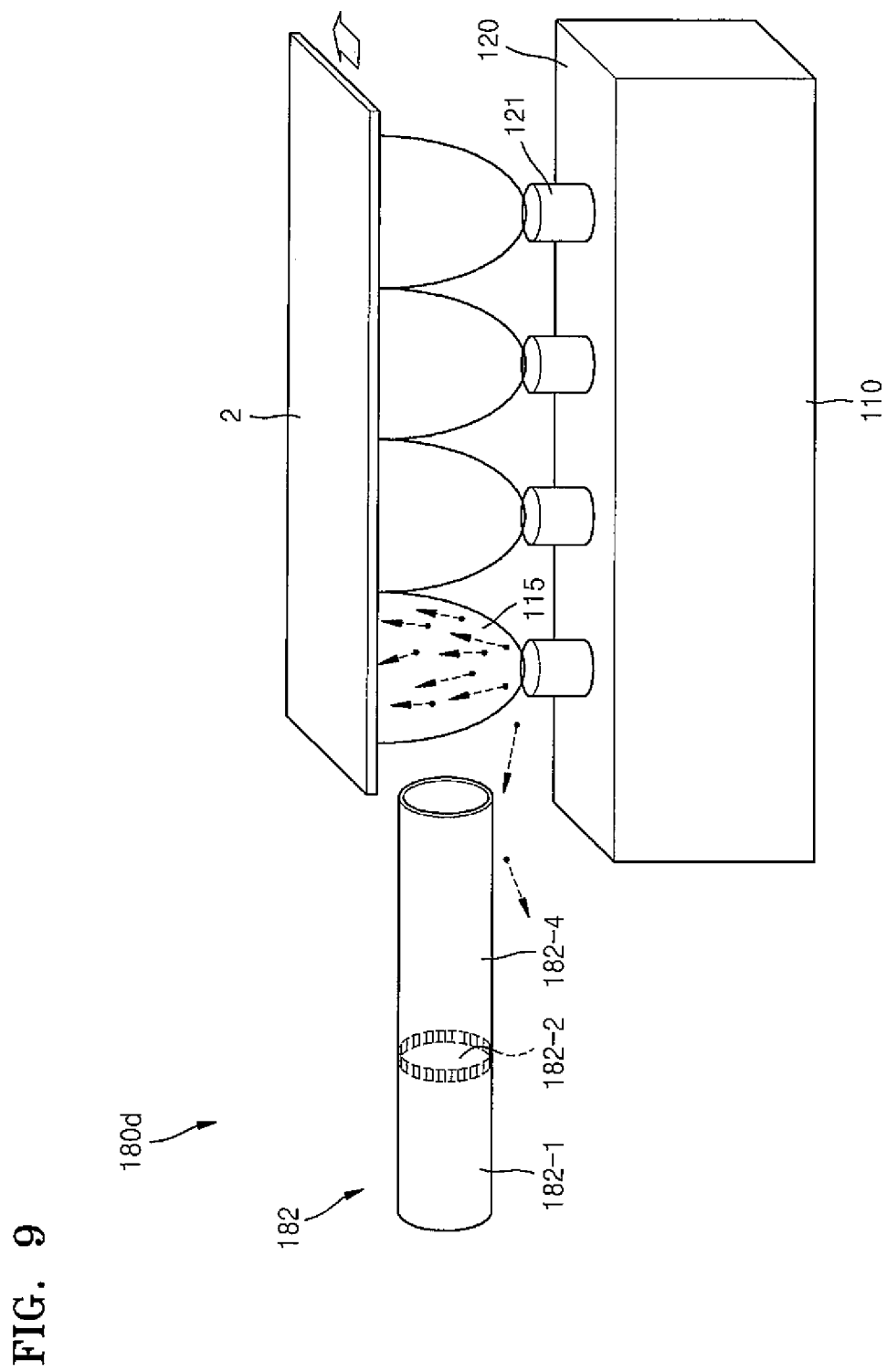
FIG. 9 is a schematic view illustrating another embodiment of the deposition rate monitoring apparatus 180, which may be used in the deposition part 100 of FIG. 3.

FIG. 9 is a schematic view illustrating another embodiment of the deposition rate monitoring apparatus 180d, which may be used in and with the deposition unit 100 of FIG. 3. Referring to FIG. 9, the deposition rate monitoring apparatus 180d according to the present embodiment includes a light source (see for example, 181 of FIG. 5), a first optical system (see for example, 182 of FIG. 5), a second optical system (see for example, 183 of FIG. 5), and a first light sensor (see for example, 184 of FIG. 5). The first optical system (see for example, 182 of FIG. 5) may include a lens 182-1, and a protective window 182-2, and the protective window 182-2 may be further formed with a cylindrical protective member 182-4.

That is, in order to prevent the deposition material from being deposited on the first optical system (see for example, 182 of FIG. 5), compared with the deposition rate monitoring apparatus in the previous embodiment shown in FIG. 5, the deposition rate monitoring apparatus 180d according to the present embodiment is characterized by further including the protective member 182-4. That is, the protective member 182-4 is formed at one side of the protective window 182-2 of the first optical system (see for example, 182 of FIG. 5) to prevent the deposition material 115 discharged from the deposition source 110 from linearly moving toward the protective window 182-2 and being deposited. In detail, since deposition molecules ballistically move within a mean free path under a high vacuum, the protective member 182-4 having a long cylindrical shape may be formed at one side of the protective window 182-2 to effectively prevent the deposition material from being deposited on the first optical system (see for example, 182 of FIG. 5).

While FIG. 9 shows that the protective member 182-4 is formed in a cylindrical shape, the spirit and scope of the present invention is not limited thereto, and the protective member 182-4 may be formed in various shapes that may prevent the deposition material from being deposited on the protective window 182-2.

Hereinafter, a deposition rate monitoring apparatus 180e of the organic layer deposition apparatus 1 according to another embodiment of the present invention will be described in more detail.

FIG. 10 is a schematic view illustrating another embodiment of the deposition rate monitoring apparatus 180e, which may be used in and with the deposition unit 100 of FIG. 3. Referring to FIG. 10, the deposition rate monitoring apparatus 180e according to the present embodiment includes a light source (see for example, 181 of FIG. 5), a first optical system (see for example, 182 of FIG. 5), a second optical system (see for example, 183 of FIG. 5), and a first light sensor (see for example, 184 of FIG. 5). The first optical system (see for example, 182 of FIG. 5) may include a lens 182-1, and a protective window 182-2.

The present embodiment is characterized by considering and evaluating attenuation of an optical signal caused by the deposition material deposited on the first optical system (see for example, 182 of FIG. 5) instead of preventing the deposition material from being deposited on the first optical system (see for example, 182 of FIG. 5). That is, an optical signal measured by the first light sensor (see for example, 184 of FIG. 5) is multiplied by a proper correction coefficient to evaluate the attenuation of the optical signal. The correction coefficient may be determined by measuring an optical signal when the protective window 182-2 exists and an optical signal when the protective window 182-2 does not exist. A ratio of the optical signals corresponding to the correction coefficient may specify an optical loss due to the protective window 182-2.

Figure 11:
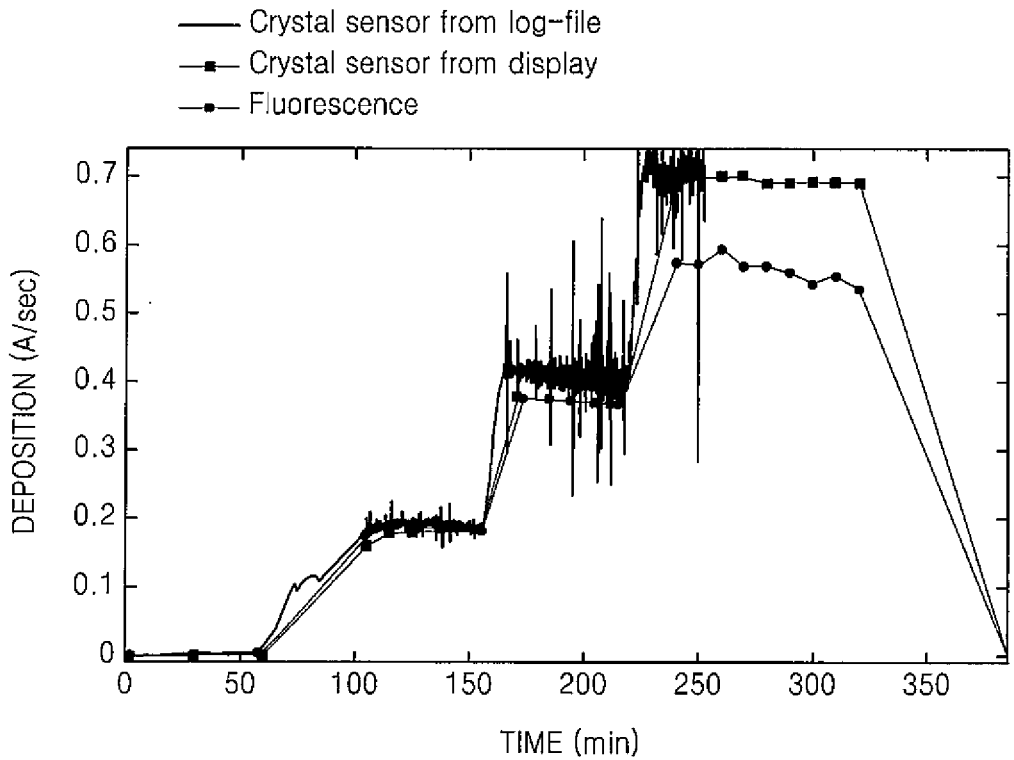
FIGS. 11 and 12 are graphs showing respective deposition rates measured by a quartz crystal monitoring (QCM) system, which is provided as a comparative example, and a fluorescence measurement method according to embodiments of the present invention.

FIG. 11 is a graph showing deposition rates measured by an existing quartz crystal monitoring (QCM) system, which is provided as a comparative example, and a fluorescence measurement method of the present invention. In FIG. 11, the horizontal axis indicates time flow and the vertical axis indicates deposition rate. Referring to FIG. 11, since the QCM system is positioned outside the flow of the deposition material and simply measures only distributed molecules, the deposition rate may be excessively measured, which becomes serious particularly when the concentration of the molecules is high.

Figure 12:
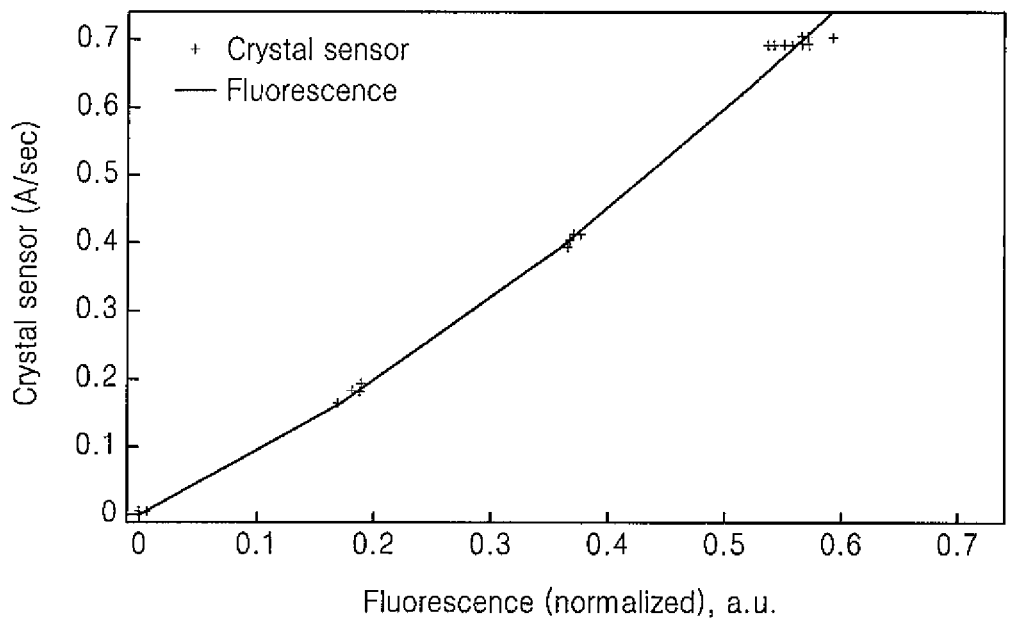

FIG. 12 is a graph showing deposition rates measured by an existing quartz crystal monitoring (QCM) system, which is provided as a comparative example, and a fluorescence measurement method of the present invention. In FIG. 12, the horizontal axis indicates the amount (atomic unit: a.u.) of the deposition material that is a fluorescent material, and the vertical axis indicates deposition rate. As seen from FIG. 12, since the measurement by the QCM is non-linear, and the QCM system is positioned outside the flow of the deposition material and simply measures only dispersed molecules, the deposition rate may be excessively measured.

According to embodiments of the present invention, the deposition rate of an organic deposition material may be monitored in real time within a response time range of not more than 100 ms. Also, embodiments of the present invention enable to measure a high sensitivity deposition rate not more than 0.005 A/sec. Further, since the upper limit of the measurable deposition rate is limited only by contamination of the protective window, a wide range of deposition measurement will be possible. Furthermore, it is possible to measure the deposition rate only with respect to a specific type of deposition material, and effects in which the measurement of the deposition rate does not depend on the inner pressure of the vacuum chamber or vapor pressure may be obtained. Moreover, since the measurement of the deposition rate is performed in a non-contact type, an effect in which contact time increases may be obtained.

As described above, according to the one or more of the above embodiments of the present invention, an apparatus for monitoring deposition rate, an apparatus for depositing an organic layer and having the monitoring apparatus, a method of monitoring deposition rate, and a method of manufacturing an organic light-emitting display device using the same that are suitable for a mass production process of a large-sized substrate and enable a high resolution patterning may be realized.

Although the present invention has been described with reference to limited example embodiments thereof, it will be understood by those of ordinary skill in the art that various changes in form and details may be made therein without departing from the spirit and scope of the present invention. Also, although not described, it should be understood that equivalent methods and apparatuses are also embraced as it is in the present invention. Therefore, the true scope of protection of the present invention is defined by the appended claims and their equivalents.

What is claimed is:

1. A deposition rate monitoring method for measuring a deposition rate of a deposition material discharged from a deposition source, the method comprising:
   emitting light having a wavelength within a photo excitation bandwidth of the deposition material from a light source;
   irradiating the light emitted from the light source toward the deposition material discharged from the deposition source; and
   detecting an amount of light emitted from the deposition material which is excited by the irradiated light,
   wherein the light emitted from the light source is irradiated toward a nozzle of the deposition source from which the deposition material is discharged.

2. The deposition rate monitoring method of claim 1, wherein the emitting of the light from the light source comprises selectively emitting only the light having a wavelength for exciting the deposition material from the light source.

3. The deposition rate monitoring method of claim 1, wherein the detecting of the light comprises detecting an amount of fluorescence emitted from the deposition material which is excited by the irradiated light.

4. The deposition rate monitoring method of claim 1, wherein the emitting of the light from the light source further comprises measuring an intensity of the light irradiated from the light source.

5. The deposition rate monitoring method of claim 4, further comprising normalizing a signal detected in the detecting of the amount of the light emitted from the deposition material which is excited by the irradiated light using a signal detected in the measuring of the intensity of the light irradiated from the light source.

6. The deposition rate monitoring method of claim 1, wherein the detecting of the amount of the light emitted from the deposition material which is excited by the irradiated light further comprises detecting amounts of lights other than fluorescence among the lights emitted from the deposition material.

7. The deposition rate monitoring method of claim 6, further comprising subtracting the lights other than the fluorescence among the lights emitted from the deposition material from the light emitted from the deposition material which is excited by the irradiated light.

8. The deposition rate monitoring method of claim 1, further comprising heating a first optical system which irradiates the light emitted from the light source toward the deposition material discharged from the deposition source.

9. A method of manufacturing an organic light-emitting display apparatus using an organic layer deposition apparatus to form an organic layer on a substrate, the method comprising:
   transferring, into a chamber, a moving unit on which the substrate is attached, by using a first transfer unit passing through the chamber;
   forming the organic layer by depositing a deposition material discharged from an organic layer deposition assembly on the substrate while the substrate is moved relative to the organic layer deposition assembly with the organic layer deposition assembly in the chamber being spaced apart from the substrate; and
   returning the moving unit separated from the substrate using a second transfer unit passing through the chamber,
   wherein the forming of the organic layer comprises:
      emitting light having a wavelength within a photoexcitation bandwidth of the deposition material from a light source;
      irradiating the light emitted from the light source toward the deposition material discharged from a deposition source; and
      detecting light emitted from the deposition material which is excited by the irradiated light,
      wherein the light emitted from the light source is irradiated toward a nozzle of the deposition source from which the deposition material is discharged.

* * * * *